USOO5858365A

United States Patent [19]
Faller

[11] Patent Number: 5,858,365
[45] Date of Patent: Jan. 12, 1999

[54] METHODS FOR THE TREATMENT OF WOUNDS USING BUTYRIC ACID SALTS AND DERIVATIVES

[75] Inventor: Douglas V Faller, Braintree, Mass.

[73] Assignee: Trustees of Boston University, Boston, Mass.

[21] Appl. No.: 473,957

[22] Filed: Jun. 7, 1995

Related U.S. Application Data

[62] Division of Ser. No. 142,908, Oct. 29, 1993, abandoned.

[51] Int. Cl.$^6$ .......................... A61K 39/00; A61K 31/19; A01N 37/00; C07H 11/00
[52] U.S. Cl. ..................................... 424/184.1; 424/278.1; 536/115; 536/119; 514/12; 514/551; 514/925; 514/926; 514/927; 514/928
[58] Field of Search .............................. 424/184.1, 85.2; 536/115, 119; 514/12, 557, 925–928

[56] References Cited

U.S. PATENT DOCUMENTS

| | | | |
|---|---|---|---|
| 3,471,513 | 10/1969 | Chinn et al. | 260/326.3 |
| 4,008,323 | 2/1977 | Cousse et al. . | |
| 4,011,336 | 3/1977 | Amann et al. . | |
| 4,031,243 | 6/1977 | Aparicio et al. | 424/317 |
| 4,058,558 | 11/1977 | Cousse et al. . | |
| 4,131,617 | 12/1978 | Esanu . | |
| 4,176,193 | 11/1979 | Esanu . | |
| 4,234,599 | 11/1980 | Van Scott et al. . | |
| 4,671,901 | 6/1987 | Green . | |
| 4,699,926 | 10/1987 | Abraham et al. . | |
| 4,704,402 | 11/1987 | Abraham et al. . | |
| 4,731,381 | 3/1988 | Abraham et al. . | |
| 4,732,914 | 3/1988 | Morton | 514/530 |
| 4,735,967 | 4/1988 | Neesby | 514/557 |
| 4,751,244 | 6/1988 | Abraham et al. . | |
| 4,822,821 | 4/1989 | Perrine . | |
| 4,925,873 | 5/1990 | Friedhoff et al. . | |
| 4,952,560 | 8/1990 | Kigasawa et al. | 514/2 |
| 5,023,251 | 6/1991 | Sattler et al. | 514/179 |
| 5,025,029 | 6/1991 | Perrine . | |
| 5,039,703 | 8/1991 | Breuer | 51/557 |
| 5,081,124 | 1/1992 | Hughes . | |
| 5,137,734 | 8/1992 | Spiegelman et al. | 424/574 |
| 5,185,436 | 2/1993 | Villa et al. . | |
| 5,208,333 | 5/1993 | Paul et al. . | |
| 5,378,716 | 1/1995 | Hamanaka et al. . | |
| 5,403,867 | 4/1995 | Okumura et al. . | |
| 5,674,912 | 10/1997 | Martin . | |
| 5,679,707 | 10/1997 | Okumura et al. . | |

FOREIGN PATENT DOCUMENTS

| | | |
|---|---|---|
| 1209037 | 8/1986 | Canada . |
| 0224599 | 6/1987 | European Pat. Off. . |
| 2126082 | 3/1984 | United Kingdom . |

OTHER PUBLICATIONS

Krantis et al., 1989, "Augmentation of Cysteamine–Induced Ulceration", *Dig. Dis. Sci.* 34(8), pp. 1211–1216.

Nagai et al., 1971, "Studies on the Synergistic Action and Anti–Ulcerous", Arzneim–Forsch, 21(1), pp. 96–97.

Bourgeade et al., 1979, "Enhancement of Interferon Anti–tumor Action by Sodium Butyrate" *Cancer Res.*, 39, pp.. 4720–4723.

M. Bugaut et al. Annu. Rev. Nutr. 13:217–41 (1993).

"Sodium n–butyrate enhancement of prostaglandin $D_2$ antitumor efficacy", *Biochemical Pharmacology*, vol. 34, No. 20, pp. 3771–3774, 1985.

T. R. Breitman et al., Combinations of retinoic acid with either sodium butyrate, dimethyl, sulfoxide, or hexamethylene bisacetamide synergistically induce differentiation of the human myeloid leukemia cell line HL60, *Cancer Research*, vol. 50, pp. 6268–6273, Oct. 1, 1990.

A. Leder et al., Differential of Erythroleukemic Cells in the Presence of Inhibitors of DNA Synthesis, *Science*, vol. 190, pp. 893–894, Jul. 14, 1975.

C. Garre et al., Regulation of Acetylcholinesterase Expression in the K–562 Cell Line, *Cancer Research*, vol. 44, pp. 3749–3751, Sep., 1984.

L. Wasserman et al., Differential Effects of Sodium Butyrate and Dimethylsulfoxide on Gamma–Glutamyl Transpeptidase and Alkaline Phosphatase Activities in MCF–7 Breast Cancer Cells, *Expl. Cell Biol.*, vol. 55, pp. 189–193, 1987.

M. Abe et al., Sodium Butyrate Induction of Milk–related Antigens in Human MCF–7 Breast Carcinoma Cells, *Cancer Research*, vol. 44, pp. 4574–4577, Oct., 1984.

N. F. Guilbaud et al., Effects of Differentiation–Inducing Agents on Maturation of Human MCF–7 Breast Cancer Cells, *Journal of Cellular Physiology*, vol. 145, pp. 162–172, 1990.

C. J. Ormandy et al., Coordinate Regulation of Oestrogen and Prolactin receptor expression by Sodium Butyrate in Human Breast Cancer Cells, *Biochemical and Biophysical Research Communications*, vol. 182, No. 2, pp. 740–745, Jan. 31, 1992.

J. R. Gum et al., Effects of Sodium Butyrate on Human Colonic Adenocarcinoma Cells, *The Journal of Biological Chemistry*, vol. 262, No. 3, p. 1092–1097, Issue of Jan. 25, 1987.

J. C. Byrd et al., Two Types of Transglutaminase in the PC12 Pheochromocytoma Cell Line, *The Journal of Biological Chemistry*, vol. 262, No. 24, pp. 11699–11705, Issue of Aug. 25, 1987.

S. H. Kim et al., Modification of thermosensitivity of HeLa Cells by Sodium Butyrate, Dibutyryl Cyclic Adenosine 3':5'–Monophosphate, and Retinoic Acid, *Cancer Research*, vol. 44, 697–702, Feb., 1984.

F. N. M. Naguib et al., Effects of N,N–Dimethylformamide and Sodium Butyrate on Enzymes of Pyrimidine Metabolism in Cultured Human Tumor Cells, *Leukemia Research*, vol. 11, No. 10, pp. 855–861, 1987.

(List continued on next page.)

*Primary Examiner*—Nita Minnifield
*Attorney, Agent, or Firm*—Kenyon & Kenyon

[57] ABSTRACT

This invention is directed to methods of administering physiologically stable and safe compositions of butyric acid salts and derivatives to a patient for the purpose of wound healing.

11 Claims, 21 Drawing Sheets

OTHER PUBLICATIONS

J. R. Cook et al., Effect of Sodium Butyrate on α–Fetoprotein Gene Expression in Rat Hepatoma Cells in Vitro, *Cancer Research*, vol. 45, pp. 3215–3219, Jul., 1985.

C. Augeron et al., Emergence of Permanently Differentiated Cell Clones in a Human Colonic Cancer Cell Line in Culture after Treatment with Sodium Butyrate, *Cancer Research*, vol. 44, pp. 3961–3969, Sep., 1984.

S. P. Langdon et al., Effect of Sodium Butyrate and Other Differentiation Inducers of Poorly Differentiated Human Ovarian Adenocarcinoma Cell Lines, *Cancer Research*, vol. 48, pp. 6161–6165, Nov. 1, 1988.

D. Tsao et al., Differential Effects of Sodium Butyrate, Dimethyl Sulfoxide, and Retinoic Acid on Membrane–Associated Antigen, Enzymes, and Glycoproteins of Human Rectal Adenocarcinoma Cells, *Cancer Research*, vol. 42, pp. 1052–1058, Mar., 1982.

A. Morita et al., Effect of Sodium Butyrate on Alkaline Phosphatase in HRT–18, a Human Rectal Cancer Cell Line, *Cancer Research*, vol. 42, pp. 4540–4545, Nov., 1982.

J. D. Newman et al., Induction of the Insulin Receptor and Other Differentiation Markers by Sodium Butyrate in the Burkitt, Lymphoma Cell, Raji, *Biochemical and Biophysical Research Communications*, vol. 161, No. 1, pp. 101–106, May 30, 1989.

C. Rius et al., The Induction of Vimentin Gene Expression by Sodium Butyrate in Human Promonocytic Leukemia U937 Cells, *Experimental Cell Research*, vol. 188, pp. 129–134, 1990.

"Abstract", D.M. McCafferty et al., Int. J. Tissue React. 1989; 11(F): 165–8.

"Abstract", J.M. Harig et al., N. Engl. J. Med. Jan. 5, 1989; 320(1): 23–8.

"Abstract", D.M. McCafferty et al., Agents Actions 1992; Spec. No.: C79–81.

"Abstract", W. Scheppach et al., Gastroenterology Jul., 1992; 103(1): 336–8.

"Abstract", W.E. Roediger et al., Lipids Oct. 1990; 25(10): 646–52.

"Abstract", R.I. Breuer et al., Dig. Dis. Sci. Feb. 1991; 36(2): 185–7.

"Abstract", P. Planchon et al., In Vivo Nov.–Dec. 1992; 6(6) 605–10.

"Abstract", P. Planchon et al., Anticancer Res. Nov.–Dec. 1992; 12(6B): 2315–20.

"Abstract", S.J. Gaudet et al., Neurochem Int. Mar. 1993; 22(3): 271–5.

"Abstract", C.D. Gerharz et al., Clin. Exp. Metastasis Jan. 1993; 11(1): 55–67.

"Abstract", D. Garsetti et al., Biochem. J. Dec. 15, 1992; 228(pt 3): 831–7.

"Abstract", T. Boulikas, Anticancer Res. May–Jun. 1992; 12(3): 885–98.

"Abstract", M.M. Belcheva et al., J. Pharmacol. Exp Ther. Oct. 1991; 259(1): 302–9.

Randy A. Hock et al., "Retrovirus–mediated transfer and expression of drug resistance genes in human hematopoietic progenitor cells", Nature vol. 320, 20 Mar. 1986, pp. 275–277.

A. Novogrodsky, et al., "Effect of Polar Organic Componds on Leukemic Cells", American Cancer Society; vol. 51, Jan. 1, 1983; pp. 9–14.

J. Leavitt et al., "Butyric acid suppression of the in vitro neoplastic state of Syrian hamster cells", vol. 271, 19 Jan. 1978, pp. 262–265.

M.C. Hoessly et al., "Factors Responsible for Variable Reported Lineages of HL–60 Cells Induced to Mature with Butyric Acid", Cancer Research, 49, Jul. 1, 1989, 3594–97.

James Watson et al., "Butyric Acid In the Treatment of Cancer", The Lancet, Apr. 8, 1993, pp. 746–748.

Hans–Peter Bartram et al., "Proliferation of Human Colonic Mucosa as an Intermediate Biomarker of Carcinogenesis: Effects of Butyrate, Deoxycholate, Calcium, Ammonia, and pH", Cancer Research, 53, Jul. 15, 1993 pp. 3283–3288.

Charles Chany et al., "Antitumor Effect of Arginine Butyrate in Conjunction with Corynebacterium Parvum and Interferon", Int. J. Cancer: 30, (1982) pp. 489–493.

Charles Chany et al., "Effect of Coordinated Therapeutic Assays Using C. Parvum, Interferon and Arginine Butyrate on Spontaneous Disease and Survival of AKR Mice", Int. J. Cancer: 32, (1993) pp. 379–383.

H. Phillip Koeffler, Induction of Differentiation of Human Acute Myelogenous Leukemia Cells; Therapeutic Implications:, Blood, vol. 62, No. 4, Oct. 1983, pp. 709–721.

Michael Reiss et al., "Induction of Tumor Cells Differentiation as a Therapeutic Approach: Preclinical Models for Hematopoietic and Solid Neoplasms", Reports, vol. 70, No. 1, Jan. 1986, pp. 201–218.

Alexander Bloch, "Induced Cell Differentiation in Cancer Therapy", Cancer Treatment Reports, vol. 68, No. 1, Jan. 1984, pp. 199–205.

M.F. Bourgeade et al., "Enhancement of Interferon Antitumor Action by Sodium Butyrate", Cancer Research, vol. 39, Nov. 1979, pp. 4720–4723.

H. Barker et al., "The Actions of Cyclic AMP, Its Butyryl Derivatives and Na Butyrate on the Proliferation of Malignant Trophoblast Cells in vitro", Br. J. Cancer, vol. 35, 1977, pp. 314–321.

Diane Garsetti et al., "Butyric acid–induced differentiation of HL–60 cells increases the expression of a single lysophospholipase", Biochem. J., vol. 288, 1992, pp. 831–837.

L. Sachs, "Cell Differentiation and Bypassing of Genetic Defects in the Suppression of Malignancy", Cancer Research, vol. 47, Apr. 15, 1987, pp. 1981–1986.

Eric J. Seifter et al., "An Outlier Theory of Cancer Curability—Tumor Cell Differentiation as a Therapeutic Goal", The American Journal of Medicine, vol. 83, Oct. 1987, pp. 757–760.

"Research in Brief: With HMBA, Differentiation Inducers Reach Clinical Trial", World Health Communications Inc. 1987, p. 15.

Judy Sutherland et al., "Induction of the Expression of HLA Class I Antigens on K562 by Interferons and Sodium Butyrate", Human Immunology, vol. 12, 1985, pp. 65–73.

"Retrovirus–Induced Changes in Major Histocompatibility Complex Antigen Expression Influence Susceptibility to Lysis by Cytotoxic T Lymphocytes", The Journal of Immunology, vol. 135, No. 4, Oct. 1985, pp. 2287–2292.

Richard T. Maziarz et al., "The Regulation of Exogenous and Endogenous Class I MHC Genes in a Human Tumor Cell Line, K562", Molecular Immunology, vol. 27, No. 2, 1990, pp. 135–142.

Richard T. Maziarz et al., "Distinct Effects of Interferony and MHC Class I Surface Antigen Levels on Resistance of K562 Tumor Cell Line", Cellular Immunology, vol. 130, 1990 pp. 329–338.

E.V. Prochownik et al., "Deregulated expression of c–myc by murine erythroleukemia cells prevents differentiation", Nature, vol. 322, Aug. 28, 1986, p. 848–850.

Randy A. Hock et al., "Retrovirus–mediated transfer and express of drug resistance genes in human hematopoietic progenitor cells", Nature vol. 320, Mar. 20, 1986, pp. 275–277.

Jeffrey Cossman et al., "Induction to Differentiation in a Case of Common Acute Lymphoblastic Leukemia" The New England Journal of Medicine, vol. 307, No. 20, Nov. 11, 1982, pp. 1251–1254.

Prasad, 1980, "Butyric Acid A Small Fatty Acid With Diverse Biological Functions", *Life Sciences*, 27, pp. 1351–1358.

Novogrodsky et al., 1983, "Effect of Polar Organic Compounds on Leukemic Cells", *Cancer*, 51, pp. 9–14.

Watson et al., 1933, "Butyric Acid in the Treatment of Cancer", *The Lancet*, Apr. 8, 1993, pp. 746–748.

Newman et al., 1989, "Induction of the Insulin Receptor and other Differentiation".

Reiss et al., "Inducting Tumor Cell Differentiation as a Therapeutic Approach", *Cancer Treatment Report*, 70(1), pp. 201–218.

Chaney et al., 1983, "Effect of Coordinated Therapeutic Assays using C Parium", Int. J. Cancer, 32, pp. 379–383.

Pouillart et al. 1992. Int. J. Cancer. 51:596–601.

Planchon et al. 1991. Int. J. Cancer. 48:443–449.

Daniel et al. 1989. Clinica Chimica Acta. 181:255–264.

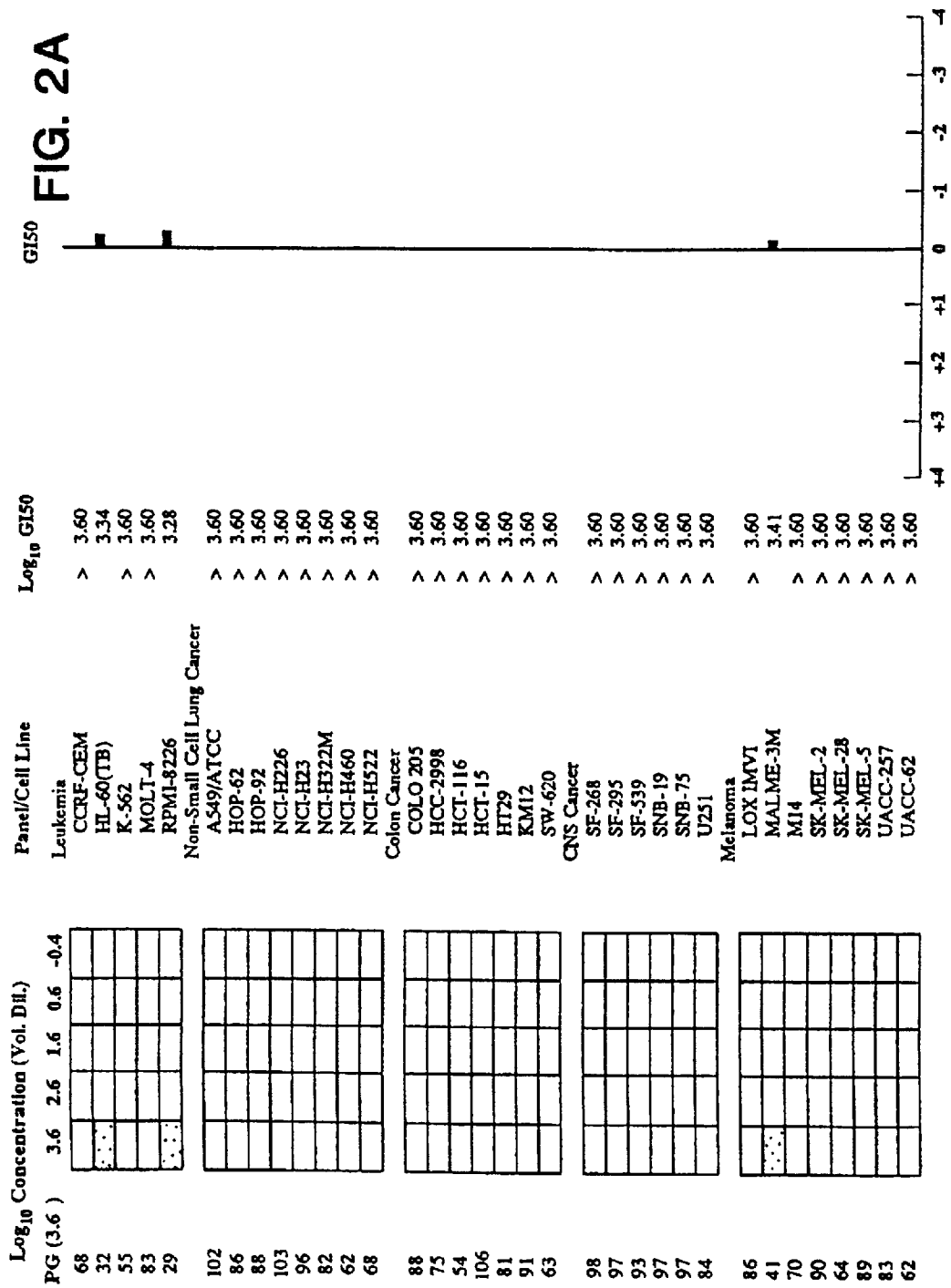

DMS 114 —○— DMS 273 —◆—

COLO 205 —●—   DLD-1 —◆—   HCC-2998 ····▲····   HCT-116 ·····□·····
HCT-15 —●—    HT29 —●—    KM12 ---▲---   KM20L2 —■—
SW-620 --●--

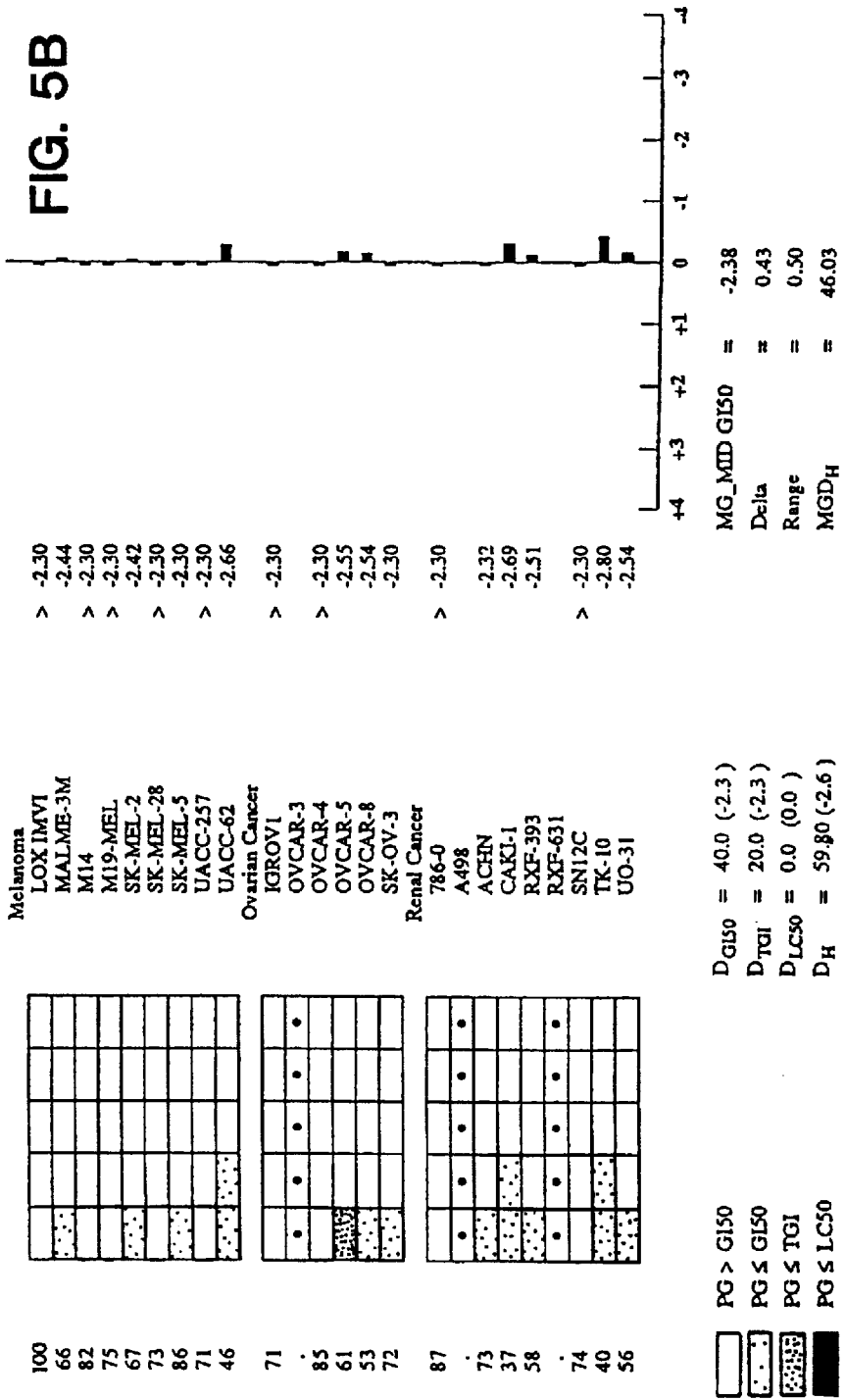

METHODS FOR THE TREATMENT OF WOUNDS USING BUTYRIC ACID SALTS AND DERIVATIVES

This application is a division of application Ser. No. 08/142,908, filed Oct. 29, 1993, now abandoned.

BACKGROUND OF THE INVENTION

1. Field of the Invention

This invention relates to the treatment of patients with neoplastic disorders using compositions containing physiologically stable compounds of butyric acid, butyric acid salts and derivatives, and combinations thereof. These compositions initiate or accelerate the differentiation of neoplastic cells and enhance the surface expression of both MHC and non-MHC antigens on transformed cells promoting their identification and clearance by the immune system. In addition, these same compositions reduce the activity of proteins associated with the development of the multi-drug resistance phenomenon, thereby increasing intracellular concentrations and the effectiveness of conventional chemotherapeutic agents.

2. Description of the Background

The most universally feared disease in the world today is cancer. Cancer has become the laymen's term for all forms of neoplasia including carcinomas, leukemias, tumors and virtually all malignancies. True cancers may better be defined as diseases which have the biological characteristics of malignant neoplasia. A neoplasm is a relatively autonomous growth of tissue, autonomous in that growth does not follow the "rules and regulations" that govern the growth of individual cells of an organism. In other words, growth is in some respect increased. A neoplasm may be benign or malignant. Benign indicates that cell growth is in some way confined, the individual cells are non-invasive and/or highly differentiated, and there is little to no anaplasia. In contrast, malignant neoplasias are non-encapsulated, invasive, and poorly differentiated, grow fairly rapidly, are anaplastic to varying degrees, and metastasize to other areas of the body. In theory, certain benign neoplasias may be early forms of a malignancy or at least a stage along the pathway to malignancy.

Any tissue of a multicellular body that is capable of cell division is capable of becoming cancerous. Cancerous or neoplastic cells act much the same as normal cells. They divide, multiple, process nutrients, perform functions characteristic of their non-neoplastic origins, and they die. Neoplasias become a health concern by carrying out these processes at a higher level effecting the normal functioning of the body. For example, neoplastic cells damage or destroy nearby organs and tissues. Healthy tissue may be out competed for space and/or nutrients by the neoplasm or by neoplastic cells which have metastasized to proximal regions of the body. Neoplasms may also have more systemic consequences effecting the regulation of specific tissues such as those of the immune system.

The basic treatment of neoplastic diseases has remained surprisingly consistent. For confined tumors such as benign hyperplasia, surgery is often suggested and the diseased tissue removed. This approach is generally preferable for otherwise healthy individuals. When the patient is not considered to be a particularly likely candidate for invasive surgical procedures and/or when the neoplasm is unconfined to a single organ or site, for example, has metastasized, drug or radiation therapy is often the only recourse. The principle idea behind these therapies is that all forms of neoplasia involve some degree of increased cell proliferation. Radiation therapy and chemotherapy are successful because they simply and indiscriminately kill multiplying cells. The problem is that not all multiplying cells are neoplastic. Most cells multiply to some degree and the variations in growth rate throughout the body are enormous. Neoplastic cells, although dividing quite rapidly, usually fall somewhere within this range. Consequently, although each of these therapies have been successful in certain contexts, they are usually not a cure.

One popular theory about the biology of cancer is that it represents an arrest in the development of the cell. The cancer cell remains in a relatively immature state and continues to be capable of growth and replication throughout its life. In contrast, a normal cell would mature fully into, for example, a functional bowel cell, blood cell or lung cell, which would not be capable of further proliferation. The normal process is called differentiation and a cancer cell could, therefore, be a cell which has not differentiated fully, quite possibly as a result of oncogene activation. In theory, agents which can force the cancer cell to complete differentiation would render it incapable of further growth and injury to the patient (E. J. Seifert et al., Am. J. Med. 83:757–60, 1987). Agents which can force differentiation of leukemia cells in vitro, such as cytosine arabinoside and retinoic acid, have recently been used effectively in patients to turn leukemia cells into normal, mature-looking cells and slow the course of the disease (L. Sachs, Cancer Res. 47:1981–86, 1987). The phorbal diester 12-0-tetradecanoylphorbol 13-acetate (TPA) has been shown to be an effective inducer of T cell differentiation in acute lymphoblastic leukemia and B cell differentiation in chronic lymphocytic leukemia (J. Cossman et al., N. Engl. J. Med. 307:1251–54, 1982). A naturally occurring tumor promoter, teleocidine B, an indole alkaloid isolated from the mycelia of Streptomyces, has been shown to have similar effects on fibroblasts (A. Bloch, Cancer Treatment Rep. 68:199–205, 1984). Unfortunately, a number of problems including the toxic nature of these inducers, the high dosages which would be required, and the potential for unwanted and dangerous side effects has compromised their usefulness (D. M. Pace et al., Canad. J. Biochem. 45:81–88, 1967).

One differentiation inducer was administered to humans as a therapy against various forms of cancer (J. Watson and M. B. Glasg, The Lancet 618:746–48, Apr. 8, 1933). Crude preparations of butyric acid and butyrate of quanine (kieselguhr and chalk) were used to treat patients suffering from carcinoma of the cervix, rectal cancer, stomach cancer, or papilloma of the ovary. In each case definitive results were undeterminable. Treatment consisted of packing the wounds after a surgical procedure with gelatin capsules containing these substances or simply applying the substance locally. However, in every case, applications were administered in conjunction with surgery and sometimes radiation therapy, both of which themselves would have had a substantial effect on tumors. With combination therapy taken into consideration, the substances had no beneficial effect. In addition, there was no information provided as to doses used or in vivo levels achieved, generally required for any determination of efficacy. Any positive effects observed could be better attributed to the ability of butyric acid to cauterize the afflicted tissue rather than any effect on malignancy. Consequently, it is impossible to determine whether butyric acid played any role and, in fact, the outcome would suggest that it had no positive effect at all.

More recently, preparations of butyric acid were shown to suppress in vitro neoplastic transformation of Syrian hamster cells (J. Leavitt et al., Nature 271:262–65, 1978). These studies demonstrated that aberrant morphology, anchorage-independent growth, and enhanced proteolytic activity, which each correlates with tumorigenicity, were all suppressed after treatments of butyric acid. However, the use of butyric acid as an anti-cancer agent was impractical and untransferable to clinical use. Butyric acid is physiologically unstable. It has an extremely short serum half-life of about two minutes and, more importantly, any biological effect requires a detectable presence. In other words, termination of treatment ends the observed biological effect making its practical application as a pharmaceutical extremely unlikely.

Sodium butyrate, a relatively nontoxic form of butyric acid, but with the same fleeting serum half-life and biological effect, has been shown to force the in vitro differentiation of human erythroleukemia cells, chronic myelogenous leukemia cells, bowel cancer cells, salivary adenocarcinoma cells, pancreatic adenocarcinoma cells, melanoma cells, ovarian adenocarcinoma cells, medullary thyroid carcinoma cells, Burkitt lymphoma cells, astrocytoma cells, and neuroblastoma cells (K. N. Prasad, Life Sci. 27:1351–58, 1980). Differentiation is tied to the expression or repression of a number of different gene products and a number of different biological activities.

For example, sodium butyrate has been shown to cause an increase in the activities of a number of mammalian enzymes in tissue culture including tyrosine hydroxylase, choline acetyltransferase, acetyl cholinesterase, adenylate cyclase in NB cells, adenosine kinase and deaminase, guanosine and adenosine monophosphate kinases, adenine and hypoxanthine phosphoribosyltransferases in human colon carcinoma cells, and sialyl transferase in HeLa cells. Alternatively, other enzymes are inhibited by sodium butyrate. Enzymes whose activities are inhibited include tyrosine transaminase in hepatoma cells, hexokinase and glucokinase in normal liver cells, and lactate dehydrogenase and pyruvate kinase in neuroblastoma cells. Also, other properties of sodium butyrate which have been demonstrated in vitro include the stimulation ganglioside $G_M1$ synthesis, induction of expression of β-adrenergic receptors and choleratoxin receptors on HeLa cells, increased production of gonadotropins, and increased synthesis of prostaglandins. Although, the mechanism(s) whereby sodium butyrate forces differentiation of tumors and arrests growth are not fully understood, sodium butyrate does increase intracellular levels of cAMP, inhibit histone acetylation, and inhibit methylation of genomic DNA. In many cases, this differentiation is also accompanied by down-regulation of activated oncogenes in the tumors, but any single specific cause and effect relationship has yet to be established.

Many studies using butyric acid have been performed on HL-60 cells, a human cell line derived from a leukemia and a commonly used myeloid progenitor line. These cells readily differentiate in the presence of about 0.5 mM butyric acid and are used to study the regulation of granulocyte differentiation and cellular metabolism (M. C. Hoessly et al., Cancer Res. 49:3594–97, 1989). Treated cells show phenotypic changes such as the accumulation of numerous granules and condensation of the nucleus (G. Rovera et al., Proc. Natl. Acad. Sci. U.S.A. 76:2779–82, 1979). In addition, transcription of the myb gene is markedly decreased in granulocytic HL-60 cells.

Sodium butyrate, as well as retinoic acid and other retenoids, certain plant lectins, phorbal esters, and cytosine arabinoside, although apparently effective in vitro, were unsuccessful or not developed for in vivo use for a number of reasons. Fairly large amounts of the substances were required to produce a meaningful effect. These levels are difficult to achieve in vivo, or would be toxic, and may produce side effects. Further, although certain agents, such as butyric acid, are fairly well tolerated on their own, the sodium salts were not. Such large amounts of the salt are required that major organ damage attributed to sodium overload was observed in animal studies.

Recent studies have indicated that the action of differentiation inducers may be somewhat definable. Dimethyl sulphoxide (DMSO) or hypoxanthine treatments of Friend leukemia cells were shown to stimulate differentiation and down regulate c-myc expression (E. V. Prochownik and J. Kukowska, Nature 322:848–850, 1986). Using recombinantly produced c-myc to inhibit the reduction of c-myc levels, differentiation of these cells was completely or partially inhibited, indicating that at least partial control of differentiation may reside at the expression of certain oncogenes. Further, as determined by others, butyrate effects the expression of a number of cellular genes. Butyric acid may only indirectly stimulate differentiation by down- or up-regulating the expression of the cellular enzymes which are the direct control. As yet, this is merely speculation and a definitive mechanism of action has still to be determined.

Current modalities for the treatment of malignancy are essentially limited to surgery, radiotherapy or chemotherapy, all of which are relatively nonspecific. Newer approaches aimed directly at the tumor cell are needed. The cellular immune system, with its striking ability to discriminate tumor cells from normal cells, is ideally suited for therapeutic manipulation. There is abundant evidence that the cellular immune system allows immuno-competent animals to reject transplanted tumors or inoculated tumor viruses. Our understanding of the immune mechanisms involved is limited, but directed manipulation of the immune response to tumors by administration of cancer vaccines or lymphokines is feasible. Still, many tumors can readily evade the cellular immune defenses. A major mechanism by which tumor cells escape from surveillance by the cellular immune system in the host is by alteration of Major Histocompatibility Complex (MHC) antigen expression. Down-regulation of MHC expression is extremely common in bowel, neuroblastoma, and small-cell lung tumors. These same tumors commonly express a mutated form of an oncogene which has been shown to down regulate MHC expression. Down-regulation, although a commonly used term, may not be correct. Tumor cells may not be capable of expressing MHC antigens like their mature, normal counterparts because of their immature, undifferentiated state.

The effector arm of the cellular immune system, comprised of cytotoxic T cells (CTL) and natural killer cells (NK), plays a pivotal role in a body's elimination of tumors. The ability to generate a CTL response to a tumor is clearly linked to the ability of an animal to reject that tumor. CTLs directed against tumors are MHC restricted to the target antigen or antigen fragments. Target antigen must be recognized on the tumor cell surface in association with MHC antigens identical, or syngeneic, to those found on the CTL itself HLA and H-2 antigens are the cell surface glycoproteins encoded by the human and murine MHC gene complexes, respectively. This requirement for a syngeneic Class I MHC antigen in association with a tumor or viral antigen is known as dual restriction. MHC expression is also likely to be regulator of tumor recognition by the natural killer arm of the cellular immune system, although its exact role is a subject of much debate. Because of their important role as restriction elements for CT-target cell recognition, the Class I MHC antigens have undergone extensive biochemical analysis. These antigens, referred to as HLA-A, -B, and -C in the human and H-2K, D and L in the mouse, are cell surfaces glycoproteins, each comprised of a polymorphic heavy chain and a non-covalently linked, non-polymorphic light chain, called $\beta_2$-microglobulin.

The remarkable dual specificity on the part of the CTL for self (syngeneic MHC) plus tumor antigen, makes it ideally suited to identify and eliminate transformed cells within the animal. Aberrant regulation of MHC expression is, however, a frequent occurrence in human tumors, allowing the tumor circumvent cellular immune surveillance by eliminating one of these two essential recognition elements. Major changes in cellular MHC expression, induced by expression of oncogenes and tumor viruses, have shown that these alterations result in biologically significant resistance to cellular immune cytotoxicity.

The recognition of virus-induced tumor antigens by the cellular immune system has been extensively examined (D. C. Flyer et al., J. Immunol. 135:2287–92, 1985). CTLs directed against sarcoma virus-induced tumor antigens are Class I-restricted. Recognition of the tumor target antigens must be in association with the appropriate syngeneic MHC gene products. Significantly, tumors induced by these viruses control their own immune recognition by direct regulation of the Class I MHC expression of the infected cells (R. T. Maziarz, et al., Mol. Immunol. 27:135–42, 1990). Recent experiments have shown that in many tumor cells, including oncogene-transformed cells, the level of MHC protein expression is so dramatically down-regulated by the infecting tumor virus that antigens cannot be recognized by CTL, which require both syngeneic MHC antigens and viral antigens on the cell surface for recognition, or by CTL lines. The level of CTL-mediated lysis of tumor cells both by MHC-restricted, virus-specific CTL and by CTL directed against allogeneic MHC determinants is directly influenced by the level of MHC Class I antigen expression on the surface of the tumor cells. Induction of the MHC antigens on the surface of the tumor cells made them once again able to be recognized and destroyed by the animal's immune system.

The human erythroleukemia cell line K562, which expresses little or no Class I MHC, is not recognized by human cytotoxic T lymphocytes. By induction of expression of Class I MHC antigens on these tumor cells using interferon, virus, sodium butyrate or transfection, new surface expression of specific Class I MHC antigens in K562 conferred upon these tumor cells susceptibility to both humoral and cellular immune recognition (R. T. Maziarz et al., Cell. Immunol. 130:329–38, 1990). This demonstrates the importance of the repression of the endogenous MHC antigens to the selective survival advantage of such tumors.

In addition to Class I MHC, other antigens are also turned on or their expression increased in the presence of butyric acid. U.S. Pat. Nos. 4,822,821, 4,997,815, 5,025,029, and 5,216,004, all of whose disclosures are specifically incorporated by reference, demonstrate that butyric acid turns on $\gamma$-globin synthesis in sickle cell and thalassemic fetal erythrocytes. Other antigens turned on by butyric acid, that are normally present on the surface of mature cells, are often missing from tumor cells. Some of these, like the IL-2 receptor, the EGF receptor or the CEA antigen, are currently being studied for the use as targets for cancer immunotherapy. For example, monoclonal antibodies coupled to diphtheria toxin and directed against the IL-2R or the EGF-R have been developed and are presently being tested. The level of IL-2R expression determines whether the tumors are susceptible to these immune-toxin therapies. Cells not expressing IL-2R are resistant. A vaccine and a toxic antibody against CEA has similarly been developed and is under investigation.

The IL-2 receptor (IL-2R) and its ligand are useful tools for biotherapeutic approaches to a number of hematopoietic malignancies. The IL-2R was first identified as a 55 kd surface peptide, p55, to which the anti-Tac ("anti-T-cell activation") monoclonal antibody bound. Later, a 75 kd peptide, p75, and a 64 kd peptide, p64, were identified in the functional IL2R complex and have since been demonstrated to be essential components of the high affinity IL-2R.

The most recent functional analysis of IL2R reveals that the receptor exists in three different isoforms: high affinity for IL-2 (dissociation constant ($K_d$) of $10^{-11}$M), intermediate affinity ($K_d$ of $10^{-9}$M), and low affinity ($K_d$ of $10^{-8}$M). Low affinity receptors consist of p55 alone and are ineffective in IL2R mediated signal transduction due to failure to internalize the bound ligand. High affinity receptors are heterotrimers (p55, p75, p64) capable of efficient ligand internalization. Intermediate affinity receptors may consist of the heterodimers p55/p75 or p75/p64. The former is capable of binding, but not internalizing ligand, thereby indicating that the p64 component is essential for receptor-mediated internalization of IL2.

Functional high affinity receptors are detected by Scatchard analysis using $I^{125}$-IL-2 on HTLV-1 associated adult T cell leukemia cells and on some chronic lymphocytic leukemia, acute lymphoblastic leukemia, and cutaneous T cell lymphoma (Sezary) cells. Because of the internalization capacity of the high-affinity IL-2R for its ligand, the concept of growth factor receptor-ligand binding as an entry point for the delivery of intracellular toxins has developed. An IL-2R-directed fusion toxin was genetically constructed and consists of a fusion of the membrane-translocating and protein synthesis-inhibiting domains of the diphtheria toxin gene to a full-length IL-2 gene, producing a recombinant protein, DAB486 IL2, capable of selectively targeting and killing high-affinity IL-2R bearing cells. When presented to cells with high affinity IL-2 receptors, the recombinant protein undergoes IL-2R-specific binding and internalization via receptor-mediated endocytosis. Processing occurs within the acidic endosome, and the A fragment of the toxin passes into the cytosol, where it inhibits protein synthesis by ADP-ribosylation of elongation factor-2, ultimately resulting in cell death. Toxin effects can be blocked with excess IL-2, with excess antibodies to IL2R, or with chloroquine which prevents endosomal acidification. A second generation IL-2 fusion toxin, referred to as DAB389-IL2, has been created in which the carboxy-terminal 97 amino acids of DAB486 are deleted, resulting in a shorter protein with a higher affinity for the IL-2R.

Based on toxin killing experiments of established cell lines using both DAB486-IL-2 and DAB389-IL 2, neoplastic cells from patients with high affinity receptors are uniformly intoxicated (minimum inhibitory concentration$_{50}$ or MIC$_{50}$ of <2.5×$10^{-10}$M), while those tumor cells without high-affinity IL2 receptors are unaffected. Previous studies involving treatment of toxin-insensitive, IL-2R negative cells with inducing agents have demonstrated in the case of PHA (phytohemagglutinin; 10 ug/ml) and bryostatin (1×$10^{-7}$M), that induction of IL2R, measured by the TAC antibody, is associated with intoxication by the fusion toxins at a MIC$_{50}$ similar to that reported for toxin-sensitive ATL cells. Clinical studies using this fusion toxin have been undertaken and clinically significant responses have been reported in 44% of patients with cutaneous T-cell lymphoma, 28% of those with low-grade and intermediate grade non-Hodgkin's lymphoma, and 15% of those with refractory Hodgkin's disease. All responding patients had IL-2 receptor-expressing tumors as measured by CD25 (TAC) staining.

While the p55 (TAC) peptide is expressed on many different hematopoietic malignancies, few other than HTLV-1 associated adult T-cell leukemia cells uniformly express the high-affinity receptor isoform. Since the Il-2R targeted fusion toxin is specifically cytotoxic only for cells expressing the high-affinity IL-2R, its therapeutic potential will be limited to those diseases in which the high-affinity receptor isoform is found. It would be very useful to extend the therapeutic potential of the IL-2 receptor-targeted fusion toxin proteins by developing physiologically inducers of the high-affinity IL-2R to convert non-expressing or low-expressing tumors to the high affinity IL-2R positive, toxin-sensitive state.

The P-glycoprotein (Pgp), encoded by the mdr-1 gene, is the protein responsible for the majority of multi-drug resistance to chemotherapeutic agents in tumors. This molecule appears to function as a pump in the cell membrane, which pumps, among other substances, certain chemotherapeutic agents out of the cell, decreasing their intra-cellular concentrations and limiting their activity.

Treatment of Pgp-expressing multidrug-resistant SW620 cell line with sodium butyrate resulted in active interference with Pgp function. After sodium butyrate treatment in SW620 human colon carcinoma cells, the intracellular accumulation of the chemotherapeutic agents vinblastine, adriamycin, and actinomycin D increased 10-fold. Sodium butyrate, while increasing Pgp levels, inhibited the phosphorylation of Pgp, and blocked the function of this drug-resistance protein.

A condition known as diversion colitis frequently develops in segments of the colorectum after a surgical diversion of the fecal stream. It persists indefinitely unless the excluded segment is reanastomosed. The disease is characterized by bleeding from inflamed chronic mucosa that mimics the bleeding of idiopathic inflammatory bowel disease, and it may culminate in stricture formation. It may represent an inflammatory state resulting from a nutritional deficiency in the lumen of the colonic epithelium and, possibly, may be effectively treated using short-chain fatty acids, the missing nutrients (J. M. Harig et al., N. Engl. J. Med. 320:23–28, 1989).

Intra-rectal butyric acid produces a consistent and reproducible colitis in mice. The severity of response observed was proportional to the concentration of butyric acid utilized. The colitogenic action of butyric acid could not be reproduced by low pH alone, or by the presence of the butyrate anion at neutral or alkaline pH (D. M. McCafferty and I. J. Zeitlin, Int. J. Tissue React. 11:165–68, 1989). However, at lower concentrations, butyric acid may have some beneficial effects. Compositions containing 80 mM acetate, 30 mM propionate, and 40 mM butyrate were used twice daily as rectal irrigations. The compositions induced improvement in nine out of ten patients with distil colitis (R. I. Breuer et al., Int. J. Colorectal Dis. 6:127–32, 1991). In another ten patient study, short-chain fatty-acid irrigations were again found to ameliorate inflammation in diversion colitis in patients unresponsive to other conventional forms of treatment. The histological degree of inflammation decreased, discharge of blood ceased, and endoscopic scores fell. On placebo, all of these parameters remained unchanged (W. Scheppach et al., Gastroenterology 103:1709–10, 1992).

SUMMARY OF THE INVENTION

The present invention overcomes the problems and disadvantages associated with current strategies and designs and provides new compositions and methods for the prophylaxis and treatment of neoplastic and other diseases and disorders.

One embodiment of the invention is directed to compositions containing physiologically stable and safe compounds comprising butyric acid salts, butyric acid derivatives and combinations thereof. Derivatives of butyric acid are compounds based on a part of the butyric acid moiety and include butyric acid analogs, homologs and next adjacent homologs, and compounds based on any of the foregoing. These compositions are useful for the treatment of human neoplastic disorders such as leukemias, lymphomas, sarcomas, neural cell tumors, carcinomas, seminomas, melanomas, neuroblastomas, mixed cell tumors, germ cell tumors, undifferentiated tumors, metastatic neoplasias, neoplasias due to infection and other malignancies.

Another embodiment of the invention is directed to methods for inducing the differentiation of neoplastic cells in patients by the administration of the above compositions. Differentiated cells have decreased growth rates, do not metastasize and eventually die thereby eliminating the neoplasm. Compositions of the invention may be administered systemically or locally to produce the desired effect.

Another embodiment of the invention is directed to methods for preventing the development of a neoplastic condition. Compositions of the invention can be administered to patients who are genetically predisposed or who have been exposed to an event which increases the probability of developing a neoplasm.

Another embodiment of the invention is directed to methods for enhancing the expression of immune-reactive MHC molecules on neoplastic cells. Cells expressing enhanced MHC antigens are better identified and recognized by the immune system of the host and efficiently eliminated. Enhanced expression of these antigens overcomes a major pathway by which many neoplastic cells escape immune system surveillance.

Another embodiment of the invention is directed to inducing the expression of cell surface non-MHC antigens such as tumor specific antigens and receptor antigens including the interleukin 2 receptor on neoplastic cells which allows for the selective targeting of diseased cells by conventional cell killing techniques and enhances the ability of the host's immune system to clear diseased cells from the body.

Another embodiment of the invention is directed to the utilization of these compositions to inhibit the process of multi-drug resistance which often occurs in the treatment of neoplastic disorders using conventional chemotherapies. Compositions of the invention act to block the mechanism whereby chemotherapeutic agents are pumped out of individual cells allowing for increased accumulations and greater effectiveness.

Another embodiment of the invention is directed to compositions and methods comprising physiologically stable and safe compounds of butyric acid salts and derivatives, or combinations thereof which are useful for wound healing. These compounds and their respective compositions stimulate cellular differentiation, tissue regeneration and possibly angiogenesis around areas of tissue damage.

Another embodiment of the invention is directed to compositions and methods containing the compounds of the invention for the treatment or prevention of gastrointestinal disorders including colitis, ulcerative colitis, inflammatory bowel disease, and Crohn's disease.

Another embodiment of the invention is directed to diagnostic kits and methods for utilizing these kits to characterize the carcinogenic or malignant potential of a patient's transformed cells.

Other embodiments and advantages of the invention are set forth in part in the description which follows, and in part, will be obvious from this description, or may be learned from the practice of the invention.

DESCRIPTION OF THE INVENTION

Figure 1A:
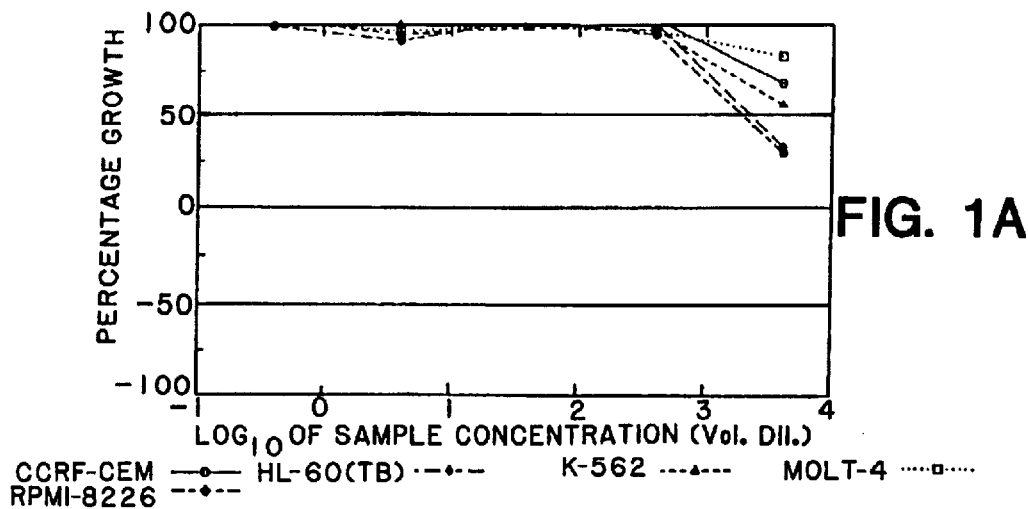
FIG. 1 Dose response curves of neoplastic cell lines treated with arginine butyrate plotted for percentage of cell growth.
Figure 1B:
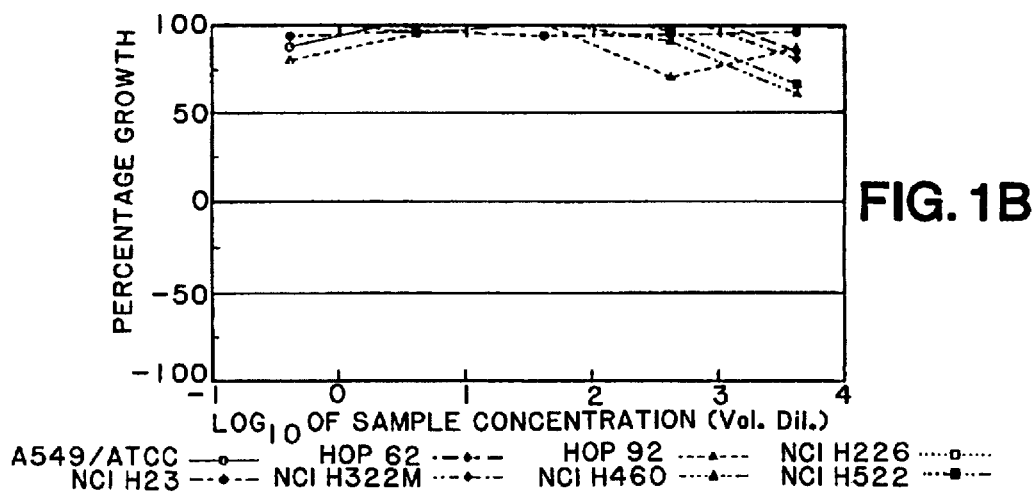
Figure 1C:
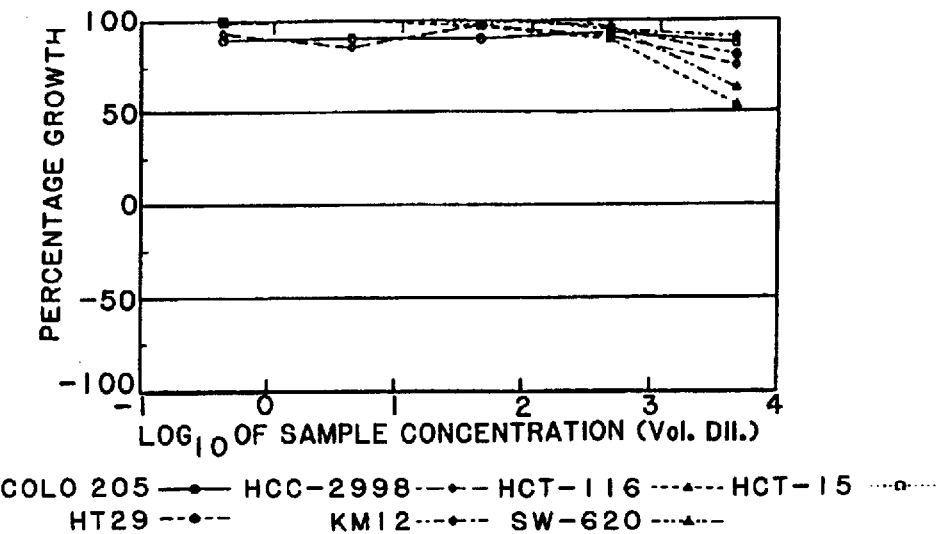
Figure 1D:
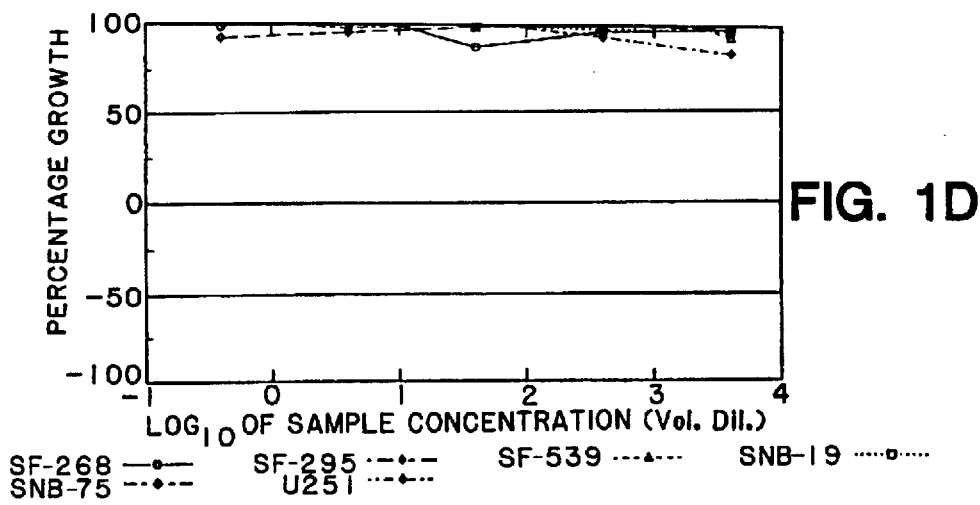
Figure 1E:
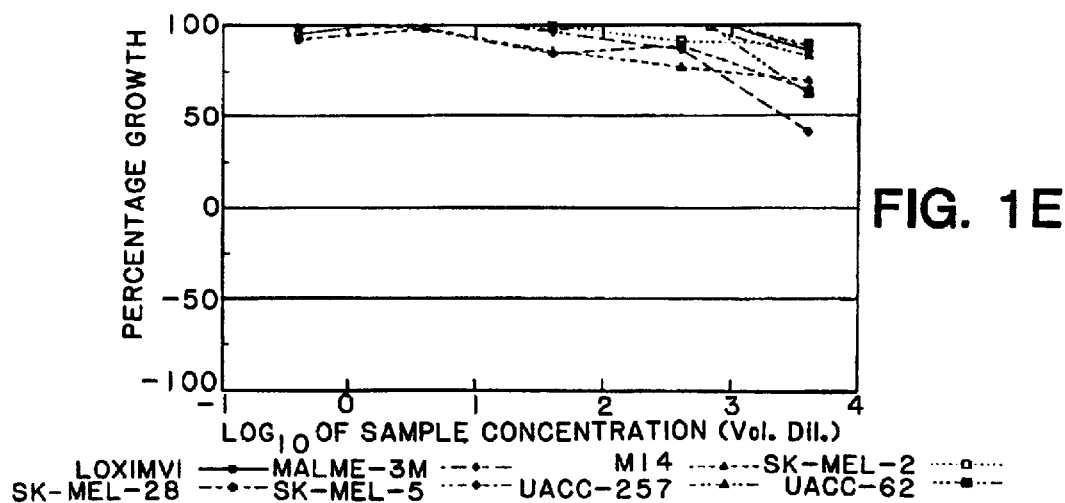
Figure 1F:
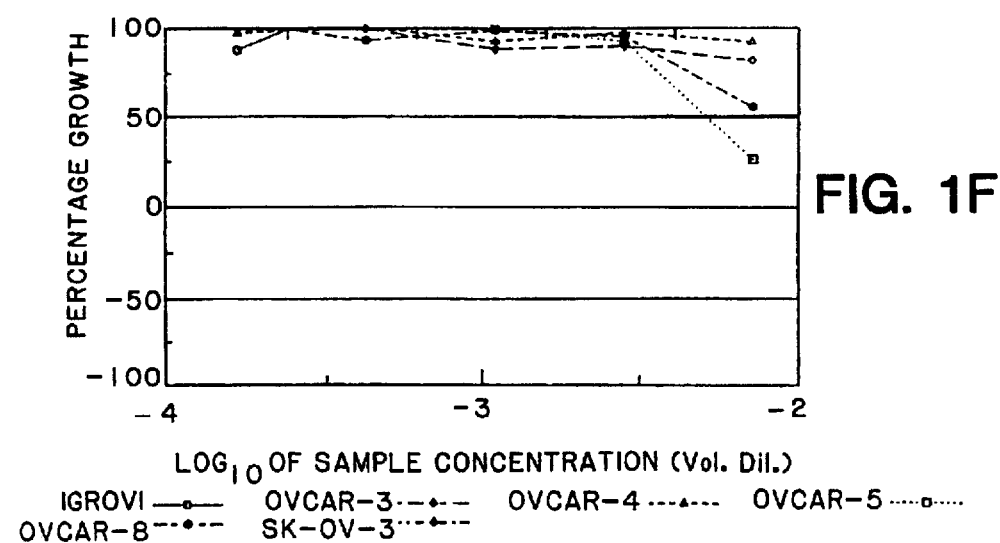
Figure 1G:
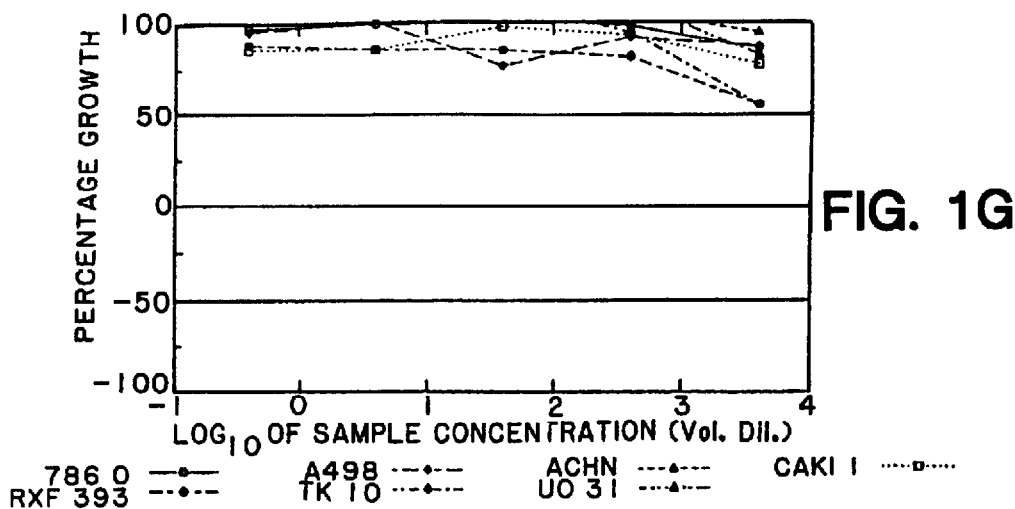
Figure 1H:
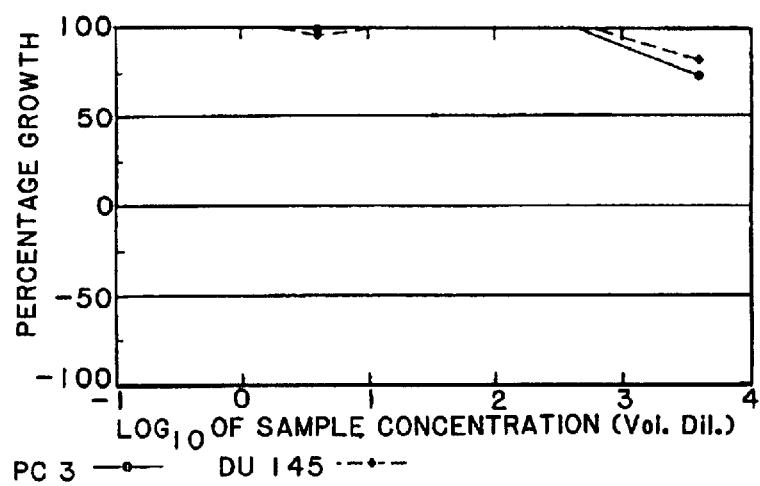
Figure 1I:
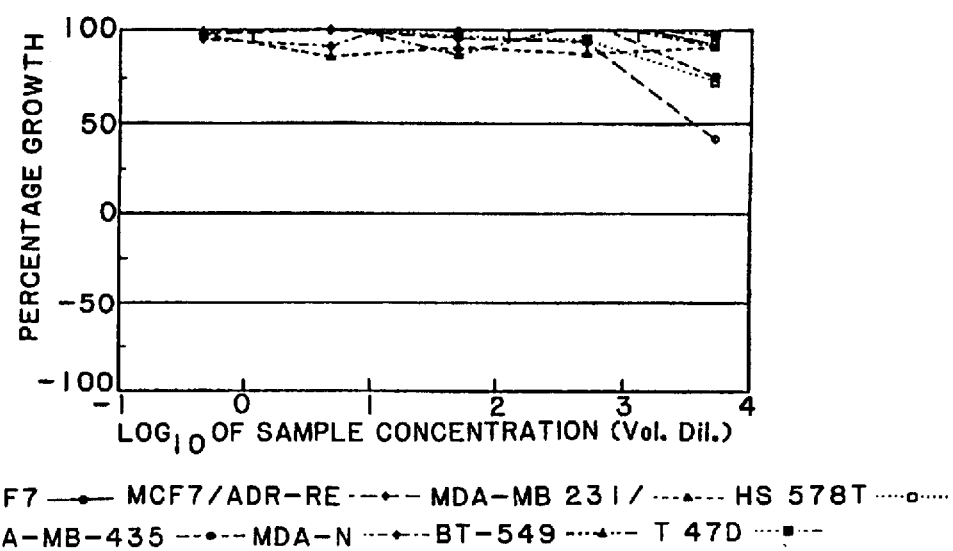

As embodied and broadly described herein, the present invention comprises compounds, compositions, and diagnostic kits containing physiologically stable compounds of butyric acid, butyric acid salts or derivatives, or combinations thereof. The invention also comprises methods for using these compounds for the prophylaxis or treatment of neoplastic and gastrointestinal disorders in patients as well as for uses related to wound healing and the diagnosis of the carcinogenic or malignant potential of transformed cells.

One embodiment of the invention is directed to compositions containing physiologically stable and safe compounds of butyric acid, butyric acid salts, derivatives of butyric acid and combinations thereof. Derivatives comprise compounds which are based on a part of the butyric acid moiety and include analogs, homologs including next adjacent homologs, and compounds based on any of the foregoing. Physiological stable forms of these compounds do not break down or otherwise become ineffective upon introduction to a patient prior to having a desired effect. Safe compounds are compounds which are non-toxic at required dosages, do not cause adverse reactions or side effects, and are well tolerated.

Butyric acid, also referred to as butanoic acid, is a four carbon fatty acid. Physiological stability can be measured from a number of parameters such as the half-life of the compound or of metabolic products derived from the compound, or by duration of observed effects on the patient. For example, sodium butyrate, the sodium salt of butyric acid, has an effective physiological stability, as measured in serum half-life, of about two minutes. This is too short to be practicable as a pharmaceutical. Physiologically stable butyric acid, butyric acid salts and derivatives have in vivo half lives of greater than fifteen minutes, preferably greater than one hour, more preferably greater than two hours, and even more preferably greater than four hours. Although a compound is stable using this criteria, its physiologically stability can also be measured by observing the duration of its biological effects such as an amelioration of patient symptoms, a reduction in size, volume or number of neoplastic cells, or an alteration in gene expression. Symptoms may include pain, fatigue, bleeding, fever, weight loss, night sweats, emesis, changes in bowel habits, swelling or mental disorientation. Genes whose expression may be altered include receptor genes such as the interleukin-2 receptor and the epidermal growth factor receptor, and genes which encode enzymes, transcription or replication factors, multi-drug resistance proteins such as the Pgp protein complex, tumor-specific antigens or MHC antigens. Preferably, the stability of compounds of the invention is determined as an in vivo half-life of greater than about 15 minutes, a serum half-life of greater than about 15 minutes, or a biological effect which continues for greater than 15 minutes after a treatment is terminated or the serum level of the compound has decreased by more than half.

For example, arginine butyrate has a serum half-life of about 15 minutes and produces biological effects such as increased expression of butyrate responsive genes within one hour after administration and often, depending on the parameter being observed, for greater than four hours. Isobutyramide appears in the plasma after oral administration and has a serum half-life of between 6.5 to 10.5 hours, depending on the dose administered. Biological effects can continue for upwards of 24 hours.

Physiologically stable compounds may be newly created compounds or previously known compounds which have not generally been considered to have or been tested for the herein described activities. New compounds are organically synthesized or created using the disclosures provided herein and/or the knowledge of one of ordinary skill in the art. Techniques such as, for example, rational drug design, can be used to create these novel compounds which are both biologically active and physiologically stable. In rational drug design, emphasis is placed on the interrelation between the chemical groups or components of a substance or the interactions between the binding of different components. For example, one component may be butyric acid or a derivative of butyric acid, and its binding partner a salt, metal, halogen or other neutralizing or stabilizing substance. Molecular models of the components are created to view the energetics between the components of a single compound and of the reaction between different compounds. The blend of geometric and algebraic approaches allows the quantitative assessment of proposed interactions. With this knowledge, the compound of interest is constructed which is designed to possess certain qualities and not others. Alternatively, physiologically stable compounds may be identified from the panoply of known compounds with the knowledge of the biologically active regions of butyric acid and the physiologically stable regions of other compounds as a guide. Compounds identified for probable use in a composition are then tested in tissue culture, in animals and, if possible, in humans for anti-neoplastic activity and physiological stability. Whether creating new compounds as described herein or recreating or reclassifying previously known compounds, some basic rules of chemistry and physics apply.

A physiologically stable compound generally exists in a state of lowest free energy. A compound may arrive at that state by one of two rather arbitrary changes. The first is by changing its physical state from a solid to a liquid (melting or dissolution) or gas (sublimation), a gas to a liquid (condensation) or solid, or a liquid to a solid (freezing or solidification) or gas (evaporation). Chemical state can be manipulated by altering the basic molecular structure of the compound or, sometimes, by altering a single chemical group. Useful alterations of physical state include the transformation of a liquid into a spray or gas, or a gas into a liquid or solid. Such physical transformations may simply provide a more effective route of administration.

The second way to alter a chemical state is by a chemical reaction such as, for example, combustion, oxidation, decomposition, and any reaction wherein atomic groupings are changed or modified. Chemical reactions which increase in vivo stability of a compound can be grouped into at least two categories, altering the molecular composition of the compound by reacting it with another compound or altering the atomic structure of the compound.

The mixing of two or more compounds to stabilize one or the other is not necessarily new. For example, acids are routinely mixed with bases to neutralize pH. Salts are mixed with ions to reduce ionic potential. Other mixtures, however, may be more novel. For example, it has been demonstrated that compound stability can be increased by mixing the desired compound with polyethylene glycol, another polymer or related substances. This has been shown to be surprisingly successful. Sometimes, a synergistic effect can occur between mixed compounds wherein the mixture results in the creation of a novel compound. This may have occurred with the combination of arginine and butyric acid. A new peak has appeared in HPLC profiles of mixtures which was not present in the individual profiles of either component. This peak may be a new and different compound, heretofore unknown, which is responsible for the observed biological effects.

The chemical structure of a compound can be altered by, for example, changing an acid to an aldehyde (butyraldehyde) or a ketone (buterone), adding or removing a methyl (methyl-butyl), ethyl (ethyl-butyl), propyl, butyl, or phenyl group, altering the ionic nature of the compound such as by the addition or substitution of a polar group (benzylacetone; $CH_3COCH_2COC_6H_5$), or a nonpolar group (neo-pentylbutyrate; $CH_3CH_2CH_2COOCH_2C(CH_3)_3$), or altering the relative placement of the carbon atoms such as, for example, forming positional isomers or stereoisomers. Positional isomers differ only in their spatial arrangement such as the exact placement of a chemical group. Positional isomers of butyric acid include isobutyric acid. Positional isomers of butyric acid derivatives include butylamine ($CH_3CH_2CHCH_3NH_2$) and sec-butylphosphonic acid ($CH_3CH_2CHCH_3PO_3H_2$). Stereoisomers differ only in configuration such as cis-trans geometrical isomers. Configurational stereoisomers of, for example, butadiene include both cis- and trans-butadiene. Configurational isomers of a homolog of butyric acid include tiglic acid and angelic acid ($CH_3CHCCH_3COOH$). As many catabolic enzymes are known to be stereospecific, if a limiting step in the catabolism of butyric acid involves the activity on such catabolic enzymes, by simply creating a stereoisomer, desired activity may be retained and stability increased.

Although these two categories of reactions overlap to some degree, because each can produce compounds which are different from the starting material. Such compounds may have properties which are somewhat different and be acted upon in a different fashion by endogenous enzymes of the host patient. The goal is to stabilize or enhance the active region of the compound by removing or altering the regions responsible for instability or to add stability to the chemicals themselves.

Butyric acid salts include sodium, potassium, calcium, ammonium and lithium, however, sodium butyrate is generally an undesirable salt because at efficacious concentrations, sodium tends to produce fluid build-up and there is eventual tissue destruction. Other salts of the invention do not have this property or, the compound of interest may be administered at lower doses, thereby minimizing any detrimental effect of sodium. Reagents which may be electrostatically or covalently bonded with butyric acid to increase physiological stability include amino acids such as arginine (arginine butyrate; ArgB), glycine, alanine, asparagine, glutamine, histidine or lysine, nucleic acids including nucleosides or nucleotides, or substituents such as carbohydrates, saccharides, lipids, fatty acids, proteins, or protein fragments. Combinations of these salts with butyric acid and butyric acid derivatives can also produce useful new compounds from the interaction of the combination.

Butyric acid derivatives are based on a part of the butyric acid moiety and comprise analogs, homologs including next adjacent homologs, and compounds based on any of the foregoing. Analogs of butyric acid include both structural and functional analogs. Functional analogs are those compounds which are functionally related to the activity of butyric acid. Structural analogs are those compounds which are related to butyric acid in the arrangement or number of carbon atoms. Related compounds include those compounds which have been modified such as by substitutions and/or additions. Isobutyramide is a structural analog of butyric acid and consists of four carbons, an amide group, and is both physiologically stable with a serum half-life of greater than one hour, and effective as an anti-neoplastic agent. Other examples of four carbon butyric acid analogs and homologs include isocrotonic acid ($CH_3CHCHCOOH$), cronton aldehyde ($CH_3CHCHCHO$), isobutyric acid (methyl-propionic acid or methyl-propanoic acid), tetrazole ($CN_4H_2$), succinic acid ($HOOC-CH_2-CH_2-COOH$), succinamide ($HOOC-CH_2-CH_2-CONH_2$), succinic acid diamide ($H_2NOC-CH_2-CH_2-CONH_2$), 4-oxobutanoic acid ($COH-CH_2-CH_2-COOH$), fumaric acid ($HOOC-CH=CH-COOH$), fumaric acid monoamide (fumaramide; $HOOC-CH=CH-CONH_2$) and diamide ($H_2NOC-CH=CH-CONH_2$), and butric anhydride (($CH_3CH_2CH_2CO)_2O$).

Next adjacent homologs of butyric acid are those compounds with one more or less carbon atom than butyric acid. These compounds have three or five carbons. Examples of next adjacent homologs which may be useful as anti-neoplastic agents include tiglic acid, isovaleric acid (($CH_3)_2CHCH_2COOH$), butyramide, 3-chloropropionic acid, 5-(2-chloroethyl)-tetrazole, alanine ($CH_3-CH(NH_2)-COOH$), β-chloro-D-alanine hydrochloride and β-chloro-L-alanine hydrochloride, propylamide sulfonate ($CH_3-CH_2-CHNH_2-SO_3H$), propyl-sulfate ($CH_3-CH_2-CH_2-SO_2$), and hexafluoropropionic acid ($CF_3-CF_2-COOF$).

Butyric acid derivatives also encompass those compounds in which there is a base or core structure which is butyric acid and through covalent modification, the number of carbon atoms is significantly greater than four such as cinnamic acid ($C_6H_5-CH=CH-COOH$; or 3-phenyl-2-propenoic acid), α-methyl cinnamic acid, hydro-cinnamic acid, 3- and 4-phenyl butyrate, di-, tri- and iso-phenyl butyrate, phenoxyacetic acid, thiophenoxyacetic acid, butyranilide, isoamyl-butyrate, and benzoyl acetone. These compounds, or their derivatives or salts, may be or have been shown in vitro to be physiologically stable and are possibly effective as anti-neoplastic agents. Compounds may also produce a synergistic effect when used in combination.

Physiologically stable butyric acid derivatives may also exist as or be created as compounds which are based on a part of the butyric acid moiety. Butyric acid derivatives include the compounds isovaline, valine, methionine and threonine, and compounds which have been modified by, for example, halogenating the compound one or more times using the elements fluorine (F), bromine (Br), chlorine (Cl), or iodine (I). Halogenated derivatives include chloropropionic acid ($CH_3$—$CH_2$—COCl), chloro-ethyl-tetrazole ($CN_4H_2$—$CH_2$—$CH_2Cl$), chloroalanine ($CH_3$—$CHNH_2$—COCl), butyrl-chloride ($CH_3CH_2CH_2COCl$), and heptafluorobutyric acid ($CF_3$—$CF_2$—$CF_2$—COOF). Derivatives can also be created by adding a sulfoxide group (butylsulfonate; $CH_3$—$CH_2$—$CH_2$—$COSO_3$), an amide group (butyramide; $CH_3$—$CH_2$—$CH_2$—$CONH_2$), an azo group (—N=N—), a thiocarbonyl group (—C=S), a quinoid group, or adding or creating a ring structure (cinnamic acid; $C_6H_5$—CH=CH—COOH). Derivatives are also formed by esterification, hydrogenation (butanol, $CH_3$—$CH_2$—$CH_2$—CHOH; biacetylene (CHCCCH), oxidation, hydration, alkylation, cyclization (tetrazole), or the addition of chemical groups containing phosphorous (P) such as a phosphate group ($PO_4$) or a phosphoric acid (butylphosphonic acid), sulfur (S) such as a sulfhydryl (—SH), sulfonic (—$SO_3H$) or a sulfate ($SO_4$) group, oxygen (O) such as a hydroxide (OH), a dioxide ($O_2$) or a trioxide ($O_3$), or nitrogen (N) such as an amide ($NH_2$; butylamine and piperidinic acid ($H_2NCH_2CH_2CH_2COOH$) or an amino ($NH_3$) group. Examples of butyric acid derivatives include amino butyric acid ($CH_3$—$CH_2$—$CH_2$—$CONH_2$; prepared as described in U.S. Pat. No. 2,572,809), isobutyramide ($CH_3$—$CH(CH_3)$—$CONH_2$), n-butyl-nitrite ($CH_3$—$CH_2$—$CH_2$—CONO; prepared as described in U.S. Pat. No. 2,739,166), butyramide or n-butyric acid monoamide ($CH_3$—$CH_2$—$CH_2$—$CONH_2$), butyronitrile ($CH_3$—$CH_2$—$CH_2$—CN; prepared as described in U.S. Pat. No. 3,062,883), α- or β-amino-n-butyric acid, succinamide or succinic monoamide (HOOC—$CH_2$—$CH_2$—$CONH_3$) or diamide ($NH_3OC$—$CH_2$—$CH_2$—$CONH_3$), butylphosphonic acid ($CH_3CH_2CH_2CH_2PO_3O_2$), butyraldehyde ($CH_3$—$CH_2$—$CH_2$—COH), phenyl-butyrate ($C_6H_5$—$CH_2$—$CH_2$—$CH_2$—COOH), butanal oxamine ($CH_3CH_2CH_2CHNOH$)), L-amino-n-butyric acid (LAB), and monobutyrin ($CH_2OH$—CHOH—$CH_2O$—$COCH_2$—$CH_2$—$CH_3$) and di-, tri-, and iso-butyrin. The disclosures of these U.S. patents are hereby specifically incorporated by reference.

Compounds may be created which, after introduction into the patient host, metabolize into active forms of butyric acid or butyric acid analogs and derivatives which have the desired effect on the patient. Similar compounds are disclosed in U.S. Pat. No. 5,185,436, whose disclosures are specifically incorporated by reference, in which esters of butyric acid are hydrolyzed in vivo to n-butyric acid or a similar structure. Compounds may also be created which metabolize in a timed-release fashion allowing for a minimal number of introductions which are efficacious for longer periods of time. Whether or not a particular chemical reaction can occur in vivo depends upon the relative stability of the products of the reaction when compared to that of the reactants, and the availability of a reaction pathway permitting conversion of the reactants into products at a reasonable rate. The stability factor, whose magnitude is expressed by the difference in free energy ($\Delta G$) between reactants and products, controls the nature of the product formed when the reaction is permitted to proceed until no further changes occur, in other words, attains equilibrium. This also controls the maximum yield of products to be obtained. The availability of a suitable reaction pathway, or the kinetic factor, determines the rate at which product formation can take place and also controls the time period for completion of the reaction.

Anti-neoplastic activity includes, for example, the ability to induce the differentiation of transformed cells including cells which comprise leukemias, lymphomas, sarcomas, neural cell tumors, carcinomas including the squamous cell carcinomas, seminomas, melanomas, neuroblastomas, mixed cell tumors, germ cell tumors, undifferentiated tumors and other malignancies. Upon differentiation, these cells loose their aggressive nature, no longer metastasize, are no longer proliferating and eventually die and/or are removed by the T cells, natural killer cells and macrophages of the patient's immune system. The process of cellular differentiation is stimulated or turned on by, for example, the stimulation and/or inhibition of gene specific transcription. Certain gene products are directly involved in cellular differentiation and can transform an actively dividing cell into a cell which has lost or has a decreased ability to proliferate. An associated change of the pattern of cellular gene expression can be observed. To control this process includes the ability to reverse a malignancy.

Genes whose transcriptional regulation are altered in the presence of butyric acid include the oncogenes myc, ras, myb, jun, abl and src. The activities of these gene products as well as the activities of other oncogenes are described in J. D. Slamon et al. (Science 224:256–62, 1984), whose disclosures are hereby specifically incorporated by reference. Anti-neoplastic activity also includes the ability to repress tumor angiogenesis through the blockade of angiogenesis factor activity, production or release, transcriptional regulation, or the ability to modulate transcription of genes under angiogenesis or growth factor or hormonal control. Either would be an effective therapy particularly against both prostatic neoplasia and breast carcinomas. Further activities which effect transcription and/or cellular differentiation include increased intracellular cAMP levels, inhibition of histone acetylation and inhibition of genomic methylation. Each of these activities are directly related to gene transcription and thus, cellular differentiation.

Compositions of the invention are prepared in solution as a liquid, spray, capsule or as a solid such as a powder or pill, as appropriate. For example, arginine butyrate is prepared by reacting arginine and butyric acid together, filtering the resulting product and diluting the final solution to a fixed percentage with water, saline, glycerol, polysaccharide, oil, or another relatively inert substance. Isobutyramide is prepared by reacting propionic acid with ammonia, and filtering the resulting product which is then stored at −20° C., 0° C., 4° C. or room temperature, for months to years without any significant loss of activity. Solid isobutyramide can be precipitated out of solution, washed in water and dried. This solid form may be processed into tablet or capsule forms or mixed or dissolved with a relatively inert liquid such as water, saline, glycerol, polysaccharide or oil. Monobutyrin is prepared as a liquid and can be stored without significant loss of activity for years. Filtrations are performed using 0.45, 0.22 and 0.1 micron filters as appropriate. Sterility of these compositions are assayed using procedures which select for growth of bacteria, fungi or yeast. Sterility may also be determined by assaying for nucleic acid content using, for example, PCR (polymerase chain reaction) technology wherein particular species of nucleic acid, if present, are amplified and detected as indicators of contamination. Purities of either the liquid or solid forms are assayed by high pressure liquid chromatography (HPLC), thin layer chromatography (TLC), gas chromatography or variations of these techniques such as fast-pressure liquid chromatography (FPLC), reverse-phase (RP) HPLC or another method which is available to one of ordinary skill in the art.

Composition are also tested, if necessary, for pyrogen using, for example, the limmulus amoebocyte lysate assay or the rabbit reticulocyte lysate assay.

The patient may be a domesticated animal such as a dog, cat, horse, cow, steer, pig, sheep, goat or chicken, or a wild animal, but is preferably a human. Administration may be to an adult, an adolescent, a child, a neonate, an infant or in utero. Administration of the composition may be short term, continuous or sporadic as necessary. Patients with a suspected or diagnosed neoplastic disorder may only require composition treatment for short periods of time or until the neoplasia has proceeded to remission or has been effectively eliminated.

In an alternative embodiment of the invention, the compositions and the compounds described above are useful as prophylactics or therapeutics for the treatment of a confirmed or suspected neoplastic disorder in a patient. For example, patients exposed to mutagens, carcinogens, radiation or other cancer producing agents may be continuously treated with compositions to inhibit the expected development of a neoplastic condition. Patients who have been genetically screened and determined to be at high risk for the future development of a neoplasia may also be administered compositions, possibly beginning at birth and possibly for life. Both prophylactic and therapeutic uses are readily acceptable because these compounds are generally safe and non-toxic.

The neoplastic disorder may be any disease or malady which could be characterized as a neoplasm, a tumor, a malignancy, a cancer or a disease which results in a relatively autonomous growth of cells. The neoplastic disorder may be a leukemia, a lymphoma; a sarcoma, a carcinoma such as a squamous cell carcinoma, a neural cell tumor, a seminoma, a melanoma, a germ cell tumor, an undifferentiated tumor, a neuroblastoma (which is also considered a carcinoma by some), a mixed cell tumor, a metastatic neoplasia, a neoplasia caused by an infection such as a virus (e.g. a human papilloma virus, Herpes Simplex virus I or II, a hepatitis virus, a human T cell leukemia virus or another retrovirus) or another malignancy. Neoplastic disorders prophylactically or therapeutically treatable with compositions of the invention include small cell lung cancers and other lung cancers, rhabdomyosarcomas, chorio carcinomas, glioblastoma multiformas (brain tumors), bowel and gastric carcinomas, leukemias, ovarian cancers, prostate cancers, osteosarcomas or cancers which have metastasized. Diseases of the immune system which are treatable by these compositions include the non-Hodgkin's lymphomas including the follicular lymphomas, Burkitt's lymphoma, adult T-cell leukemias and lymphomas, hairy-cell leukemia, acute myelogenous, lymphoblastic or other leukemias, chronic myelogenous leukemia, and myelodysplastic syndromes. Additional diseases treatable by the compositions include breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas and adenocarcinomas.

The composition may be administered by oral, parenteral, sublingual, rectal or enteral administration, or by pulmonary absorption or topical application. Parenteral administration may be by intravenous injection, subcutaneous injection, intramuscular injection, intra-arterial injection, intrathecal injection, intra peritoneal injection or direct injection or other administration to the site of the neoplasm. Injectable forms of administration are sometimes preferred for maximal effect. When long term administration by injection is necessary medi-ports, in-dwelling catheters, or automatic pumping mechanisms are also preferred wherein direct and immediate access is provided to the arteries in and around the heart and other major organs and organ systems.

An effective method of administering the composition of the neoplastic site may be by transdermal transfusion such as with a transdermal patch, by direct contact to the neoplasm, if accessible, such as a melanoma or other skin tumor, or by administration to an internal neoplasm through an incisions or some other artificial opening into the body. Compositions may also be administered to the nasal passages as a spray. Diseases localized to the head and brain area are treatable in this fashion as arteries of the nasal area provide a rapid and efficient access to the upper areas of the head. Sprays also provide immediate access to the pulmonary system and are the preferable methods for administering compositions to these areas. Access to the gastrointestinal tract is gained using oral, enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months.

Orally active compositions are more preferred as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or modifying the compound with a neutralizing chemical group. Oral bioavailability is also a problem because drugs are exposed to the extremes of gastric pH and gastric enzymes. These problems can be overcome in a similar manner by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

When the composition is administered orally, it may be in the form of a liquid, a pill, a tablet or a capsule. Liquids administered orally may include flavoring agents such as mint, cherry, guava, citrus, cinnamon, orange, mango, or mixed fruit flavors. Pills, capsules or tablets administered orally may also include flavoring agents. Additionally, all compositions may further comprise agents to increase shelf-life, such as preservatives, anti-oxidants and other components necessary and suitable for manufacture and distribution of the composition.

Administration by any method can be accurately quantitated by measuring levels of the composition from a sample of bodily fluid such as blood, serum or plasma. Effective serum levels of butyric acid salts, analogs, or derivatives are between about 0.01 $\mu$M to about 5.0 mM, preferably between about 1.0 $\mu$M to about 0.5 mM, more preferably between about 0.1 mM to about 0.4 mM and even more preferably about 0.2 mM. When applied by direct contact, effective levels of active ingredient may sometimes be analyzed by determining concentration of the composition in the areas which are in close contact with the area of application. For example, when applied topically to the skin, effective levels may be determined from fluid or tissue samples of the dermal tissues within a few centimeters under the area of application. In such cases, composition strength may be predetermined and used as a concentrated solution. Composition solutions of butyric acid, butyric acid salts, analogs, derivatives, or combinations thereof are between about 0.001% to 10.0%, but may be further diluted as necessary for prolonged direct contact with skin or other bodily tissues.

Compositions of the invention contain physiologically stable forms of butyric acid, butyric acid salts, analogs or derivatives, or combinations thereof, as agents which enhance the expression of the immune-reactive major histocompatibility (MHC) molecules on neoplastic cells. These enhanced MHC expressing cells are better identified and recognized by the immune system of the host and can be eliminated. Enhanced expression of surface antigens completely overcomes a major pathway by which many neoplastic cells escape the immune surveillance system. MHC antigens which have enhanced expression include the Class I, Class II and, the so-called Class III, or compliment components. Most are coded within the MHC genetic region which is located on chromosome 17 of the mouse and chromosome 8 in humans. The human MHC antigens, also referred to as the HLA complex, comprise the HLA-A, -B, and -C antigens.

Class I MHC antigens are present on the surface of all nucleated cells and are responsible for the recognition of target cells by cytotoxic T cells. Target cells in this context are virally and bacterially infected cells, graft cells expressing non-MHC antigens, damaged cells, and transformed cells. MHC encoded antigens are highly polymorphic glycoprotein chains with a molecular weight of around 40,000 to 60,000 daltons in humans. Associated with the glycoprotein chain is a smaller peptide with a molecular weight of about 12,500 daltons in humans called $\beta_2$ microglobulin which, in contrast to the MHC coded glycoproteins, is not polymorphic. Although most loci which code for Class I antigens are within the MHC genetic region, there are a number of very similar molecules such as the Qa locus in the mouse which are separate.

Class II MHC antigens are found on a large variety of cells which present antigen to T cells such as the helper T cells and the other antigen presenting cells (APC). Each Class II MHC antigen consists of two peptides of molecular weights of about 20,000 to 40,000 daltons, both of which are highly polymorphic. Immature class II molecules are often found associated with another antigen called the invariant gamma ($\gamma$) chain. Class II antigens can be found on cells such as splenic and bone marrow macrophages, B cells, lymphoid dendritic cells, Langerhan's cells, Kupffer cells, natural killer cells, astrocytes, certain endothelial cells, and certain dermal fibroblasts. A number of components of the compliment cascade including C2, C4, and factor B are encoded within the MHC in both man and mice and are often referred to as the Class III MHC molecules. Their functions are involved in several immune reactions, but these antigens are quite dissimilar from the classical Class I and II antigens.

Compounds of the invention further induce the expression of cell surface, non-MHC antigens including cell surface receptors, major histocompatibility antigens, tumor-specific antigens, interleukin (IL) receptor antigens such as the IL-2 receptor (IL-2R) and other cytokine receptors, multidrug resistance protein complexes such as Pgp protein, and growth factor receptors such as the epidermal growth factor (EGF) receptor. Certain forms of cancer also exhibit tumor-specific antigens which are normally not found on the surface of non-cancerous cells, but whose expression may also be induced or increased in the presence of butyric acid salts or derivatives. Compositions containing physiologically stable forms of butyric acid, butyric acid salts or derivatives, or combinations thereof, enhance the ability of the host's immune system to clear diseased cells from the body by stimulating the expression of these non-MHC antigens as well. Enhanced expression of tumor-specific antigens would also greatly increase the effectiveness of antibody therapy such as toxin conjugated or drug conjugated monoclonal antibodies.

In another embodiment of the invention, compositions of the invention may be used in any embodiment described herein in combination with other agents to maximize the effect of the compositions in an additive or synergistic manner. Cytokines which may be effective in combination with the compositions of the invention include growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), platelet derived growth factor (PDGF) nerve growth factor (NGF), stem cell factor (SCF), and transforming growth factor (TGF). These growth factors plus a composition may further stimulate cellular differentiation and/or the expression of certain MHC antigens or tumor antigens. For example, BCGF plus a composition may be effective in treating certain B cell leukemias. NGF plus a composition may be useful in treating certain neuroblastomas and/or nerve cell tumors. In a similar fashion, other agents such as differentiating agents may be useful in combination with a composition of the invention to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

Alternatively, other cytokines and related antigens in combination with a composition may also be useful to treat or prevent certain neoplasias. Potentially useful cytokines include tumor necrosis factor (TNF), the interleukins IL-1, IL-2, Il-3, IL-4, IL-5, IL-6, etc., the interferon (IFN) proteins IFN-$\alpha$, IFN-$\beta$, and IFN-$\gamma$; cyclic AMP including dibutyryl cyclic AMP, hemin, hydroxyurea, hypoxanthine, glucocorticoid hormones, dimethyl sulfoxide (DMSO), and cytosine arabinoside. Therapies using combinations of these agents would be safe and effective therapies against malignancies and other forms of cancer. Combinations of therapies may also be effective in inducing regression or elimination of a tumor or some other form of cancer such as compositions of the invention plus radiation therapy, toxin or drug conjugated antibody therapy using monoclonal or polyclonal antibodies directed against the transformed cells, gene therapy or specific anti-sense therapy. Effects may be additive, logarithmic, or synergistic, and methods involving combinations of therapies may be simultaneous protocols, intermittent protocols or protocols which are empirically determined.

Another embodiment of the invention comprises compositions and methods for the treatment of neoplastic disorders by augmenting conventional chemo-therapy, radiation therapy, antibody therapy, and other forms of therapy. Compositions containing physiologically stable forms of butyric acid salts or derivatives, or combinations thereof, in combination with chemotherapeutic agents, enhance the effect of the chemotherapeutic agent alone. Compositions decrease the expression or activity of proteins responsible for lowering the intra-cellular concentration of chemotherapeutic agents. Proteins responsible for resistance to drugs and other agents, the multi-drug resistance (MDR) proteins, include the P-glycoprotein (Pgp) encoded by the mdr-1 gene. Consequently, conventional drugs for the treatment of neoplastic disorders accumulate at higher concentrations for longer periods of time and are more effective when used in combination with the compositions herein. Some conventional chemotherapeutic agents which would be useful in combination therapy with compositions of the invention include the cyclophosphamide such as alkylating agents, the purine and pyrimidine analogs such as mercapto-purine, the vinca and vinca-like alkaloids, the etoposides or etoposide like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as antiinsulin and antiandrogen, the antiestrogens such as tamoxifen an other agents such as doxorubicin, L-asparaginase, dacarbazine (DTIC), amsacrine (mAMSA), procarbazine, hexamethylmelamine, and mitoxantrone. The chemotherapeutic agent could be given simultaneously with the compounds of the invention or alternately as defined by a protocol designed to maximize drug effectiveness, but minimize toxicity to the patient's body.

Another embodiment of the invention is directed to compositions and methods comprised of butyric acid salts, derivatives and combinations which are useful in wound healing. These compositions accelerate and enhance the positive resolution of bedsores, lesions, abrasions, and incisions due to surgical and other medical intrusions into a patient's body even after other conventional therapies have failed. The resolution of tissue damage includes stimulation of cellular differentiation, tissue regeneration and angdrogenesis around areas of tissue damage. These compositions would be a preferred method of treatment in many situations as neoplastic patients often have complications due to their disease or as a consequence of treatment. Compositions can be directly administered to the wound, systemically administered such as by injection, or orally administered as a liquid, capsule or pill. In addition, compositions may be absorbed onto pads, such as wound dressings and bandages, for prolonged therapy, or deposited onto objects to be inserted into or near the patient's wound for prophylaxis therapy.

Compositions of the invention are also useful for the treatment or prophylaxis of gastrointestinal disorders including colitis, inflammatory bowel disease, Crohn's disease, and ulcerative colitis. Disorders may be caused by infections, nutritional disorders, or unknown or unidentified causes. The compositions of the invention are generally more useful for the treatment of disorders of the gastrointestinal system which are more distally oriented.

Compositions are administered by oral or enema formulations, or by rectal irrigation to maximize their contact with and effectiveness on the gastrointestinal system. Dosages are between about 1 to about 12% (vol/vol) or between about 1 to about 100 mM. Doses are administered between about two to about four times a day until symptoms improve or resolve. Multiple and frequent dosing is not problematic because the compounds of the invention are safe and physiologically stable. Positive effects of treatment include a decrease of stool evacuation frequency, stool volumes, or blood loss. Endoscopic evaluation of the mucosal wall may also improve as demonstrated by visual indications and resolution of inflammation.

Another embodiment of the invention is directed to diagnostic assays or kits for determining the stage or level of severity of a particular neoplasia and that cancer's susceptibility to drug, radiation or some other form of treatment. Cells from a patient can be removed and placed in tissue culture conditions. To the cell culture, and a control culture (positive and/or negative control cells) which may be a cell line, primary cells or non-neoplastic cells from the same or a different patient, is added a compound of the invention. The compound treated culture and the control culture are incubated for a period of time, preferably one day, more preferably one to six hours and still more preferably less than one hour. The cultures are examined after the incubation period and the amount of cell division, cell proliferation, DNA replication, DNA, RNA, or protein synthesis, or the expression of cytokines, cytokine receptors, other cell surface molecules or other antigens, or other metabolic activity determined. The greater the effect on activity as compared to controls, the greater the likelihood that the particular form of cancer being examined will require aggressive treatment. Such assays would be widely useful as diagnostic tools in determining the best course of treatment for a particular patient, and also for screening new compounds for possible therapeutic or prophylactic use. It is relatively non-invasive, inexpensive, quantitative, and relatively rapid. Panels of organ-specific or other type-specific leukemic, cancerous, and other forms of transformed cells (type I-V cancers) could be tested and used to create a chart or table of cancer severity verses chemotherapeutic effectiveness from which treatments for unknown cancers can be effectively assessed. In this manner, therapeutic drugs can be more carefully selected with the effect and final outcome determined with a good deal of certainty and little risk.

The following examples illustrate embodiments of the invention, but should not be viewed as limiting the scope of the invention.

EXAMPLES

Example 1

Preparation of Compounds

Arginine butyrate for injection was prepared at 1 g/ml by weight. Anhydrous L-arginine (Aldrich Chemical Co. (St. Louis, Mo.) was combined with butyric acid, pH 5.0–5.5, in sterile nonpyrogenic water and resulted in a hypertonic solution. This solution was filtered through a 0.45 micron Nalgene filter (Nalge Co.; Rochester, N.Y.) and a 0.2 micron Nalgene filter. During transfer to sterile bottles for patient administration, the preparation was filtered a third time again through a 0.2 micron Nalgene filter. As a hypertonic solution, it should be infused directly through a long or deep intravenous access to avoid peripheral venous irritation. Stability testing determined that the drug was stable for at least 28 days (the longest period tested). Initial dosing schedules for patients is expected to be at 250 mg intervals between 500–2,000 mg/kg body weight per day for 14 days.

Isobutyramide oral solution (100 mg/ml) included 0.1% sodium benzoate (USP) as a preservative, and simple syrup (38% sucrose final concentration). Artificial cinnamon-mint flavoring (USP) was also added to increase palatability. This solution was filtered and tested for sterility and pyrogenicity.

Example 2

Induction of In vitro Differentiation

A large number of human and murine, primary and continuous cell cultures were maintained in vitro under the culturing conditions required for each cell type or cell line. A list of these cells is provided in Table I.

TABLE I

| | |
|---|---|
| Rhabdomyosarcoma | Fibroblasts (normal human) |
| Osteosarcoma (HOS) | Fibroblasts (mouse BALB/c-3T3) |
| Choriocarcinoma (JAR) | Lymphocytes (human, in MLR) |
| Glioblastoma Multiformi | Gastric Carcinoma (AGS) |
| Myeloid Leukemia (HL60) | Erythroleukemia (K562) |
| Colonic Adenocarcinoma (HT29) | Neuroblastoma (SK-N-MC) |

Briefly, cells were maintained in tissue culture flasks in DMEM or RPMI-1640 supplemented with 5–10% fetal bovine or calf serum. Cells were passed as needed. Butyric acid salts or derivatives (Table II) were added to an equal number of cells of each culture over a range of concentrations.

TABLE II

| Butyric Acid Salts, Analogs and Derivatives | |
|---|---|
| Sodium butyrate (NaB) | Isobutyramide (IBA) |
| Arginine butyrate (ArgB) | Monobutyrin (MoB) |
| 5-(2-chloroethyl)-tetrazole (575664) | L-amino-n-butyric acid (LAB) |
| Heptafluorbutyric acid (907388) | $CH_3-CH_2-CHNH_2-SO_3H$ (016249) |
| 3-chloropropionic acid (901409) | $CH_3-CH_2-CH_2-SO_2$ (428494) |
| β-chloro-D-alanine hydrochloride (D-594516) | $CH_3-CH_2-COOH$ (103038) |
| β-chloro-L-alanine hydrochloride (L-594515) | 4-phenyl butyrate |
| Isobutyric acid (methyl propionic acid) | Butyronitrile |
| Fumaric acid | Cinnamic acid |
| Succinamide | D-amino-n-butyric acid (DAB) |
| α-methyl-cinnamic acid | Fumaric acid monoamide |
| 3-phenyl butyrate | Phenyl acetate |
| Tributyrin (TriB) | |

All experiments were done with parallel controls of no added substances, and against a standard of sodium butyrate treatment. Results in minimum inhibitory concentration (MIC) were tabulated and are shown in Table II. Growth and morphology were evaluated on a daily basis. Where appropriate, a number of different serum concentrations were also utilized. Butyric acid solutions were prepared at 5 mM and diluted two-fold to 5 $\mu$M. Some compounds were not inhibitory at concentrations up to 5000 $\mu$M. For example, 575664 had no inhibitory effect on any cell or cell line at concentrations up to 5 mM.

TABLE III

| Cells | Compound | MIC | Compound | MIC |
|---|---|---|---|---|
| Non-Tumor: | | | | |
| Fibroblasts (normal human) | NaB | >5000 $\mu$M | ArgB | >5000 $\mu$M |
| | 901 | 5000 $\mu$M | MoB | >4000 $\mu$M |
| | D-594 | 5000 $\mu$M | | |
| Fibroblasts (Balb/c-3T3) | NaB | >5000 $\mu$M | MoB | >5000 $\mu$M |
| | 901 | 5000 $\mu$M | ArgB | >5000 $\mu$M |
| Human Tumors: | | | | |
| Rhabdomyosarcoma | NaB | 156 $\mu$M | L594 | <78 $\mu$M |
| | ArgB | 156 $\mu$M | 103 | 1250 $\mu$M |
| | MoB | 156 $\mu$M | D-594 | 2500 $\mu$M |
| | 901 | <39 $\mu$M | IBA | 30 $\mu$M |
| Osteosarcoma (HOS) | NaB | 312 $\mu$M | 901 | 78 $\mu$M |
| | ArgB | 312 $\mu$M | L-594 | N.D. |
| | MoB | 312 $\mu$M | IBA | 60 $\mu$M |
| Choriocarcinoma (JAR) | NaB | 156 $\mu$M | 901 | <78 $\mu$M |
| | ArgB | 156 $\mu$M | $\mu$594 | N.D. |
| | MoB | 156 $\mu$M | IBA | 32 $\mu$M |
| Glioblastoma Multiform | NaB | N.D. | 901 | 156 $\mu$M |
| | ArgB | 1000 $\mu$M | L-594 | N.D. |
| | MoB | 1000 $\mu$M | IBA | 312 $\mu$M |
| Colonic Adenocarcinoma (HT29) | NaB | 2000 $\mu$M | 901 | 312 $\mu$M |
| | ArgB | 2000 $\mu$M | L-594 | N.D. |
| | MoB | 2000 $\mu$M | IBA | >5000 $\mu$M |
| Gastric Carcinoma (AGS) | NaB | 2000 $\mu$M | 901 | 312 $\mu$M |
| | ArgB | 2000 $\mu$M | L-594 | |
| | MoB | 2000 $\mu$M | IBA | 312 $\mu$M |
| Myeloid Leukemia (HL 60) | NaB | 78 $\mu$M | L-594 | <78 $\mu$M |
| | ArgB | 78 $\mu$M | 907 | 625 $\mu$M |
| | MoB | 78 $\mu$M | IBA | 16 $\mu$M |
| Erythroleukemia (K562) | NaB | >5000 $\mu$M | 907 | >5000 $\mu$M |
| | ArgB | 1250 $\mu$M | L-594 | 5000 $\mu$M |
| | MoB | 1250 $\mu$M | IBA | 275 $\mu$M |
| | 901 | 1250 $\mu$M | | |

(N.D. = not done)

Example 3

Effects of Compounds on Human Neuroblastoma Cells

Human Neuroblastoma cells, SK-N-MC, were incubated in the presence of different butyric acid salts and derivatives. These cells were grown for four weeks during exposure and final cell numbers determined. Results are shown in Table IV.

TABLE IV

| Compound | Concentration | Cell Number |
|---|---|---|
| No treatment | — | $1 \times 10^8$ |
| 3-Phenyl Butyrate | 1.00 mM | $1 \times 10^8$ |
| Phenylacetate | 1.00 mM | $1 \times 10^8$ |
| Arginine Butyrate | 0.05 mM | $1 \times 10^5$ |
| Arginine Butyrate | 1.00 mM | $<1 \times 10^3$ |
| Isobutyramide | 0.05 mM | $<1 \times 10^3$ |

Dramatic decreases in cell growth were observed after treatment with either arginine butyrate or isobutyramide at levels of drug readily achieved in plasma. The expression of the oncogene n-myc was also decreased approximately three-fold in neuroblastoma cells treated with arginine butyrate (1 mM) compared to normal cells. Cells treated with phenyl butyrate or phenyl acetate showed no decrease compared to untreated cells indicating that the effect on growth was specific.

Example 4

Effect of Compounds on Human Tumor Cell Lines

Myeloid Leukemia (HL60) cells responded to butyric acid salts or derivatives by differentiation along myeloid lines. Cells acquired a number of characteristics of mature, terminally differentiated neutrophils, including the morphology of mature neutrophils, stimulation of expression of myeloperoxidase and other specific esterases, and the capacity to generate an oxidative burst. Erythroleukemia (K562) cells acquired the capacity to synthesize globin and hemoglobin, like a normal red blood cell, and actually became red in color.

Colonic adenocarcinoma cells (HT29) were treated with butyric acid salts or derivatives. These compounds affected cell growth and produced absolute growth arrest by day 3–4, with no further growth after 25 days. Inhibition of DNA synthesis (as measured by $^3$H-thymidine incorporation) occurred by 6 hrs. Expression of a proto-oncogene, a mature brush border, and the sucrase and isomaltose genes were all pronounced. Gastric carcinoma (AGS) cells expressed mucin after treatment, a marker of a mature gastric cell.

Figure 2B:
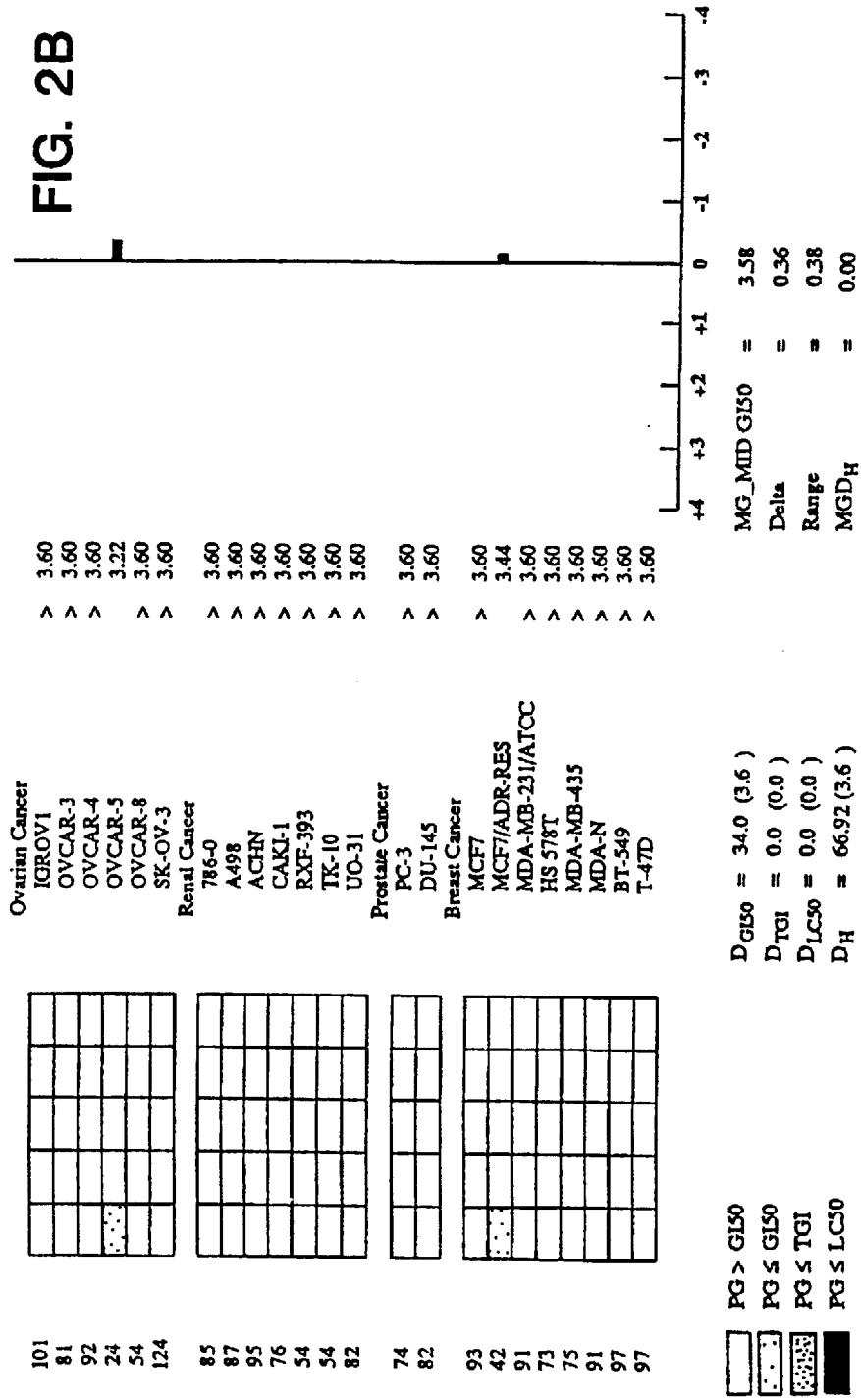
FIG. 2 Data from growth response curves indicating growth inhibition with arginine butyrate.
Figure 3A:
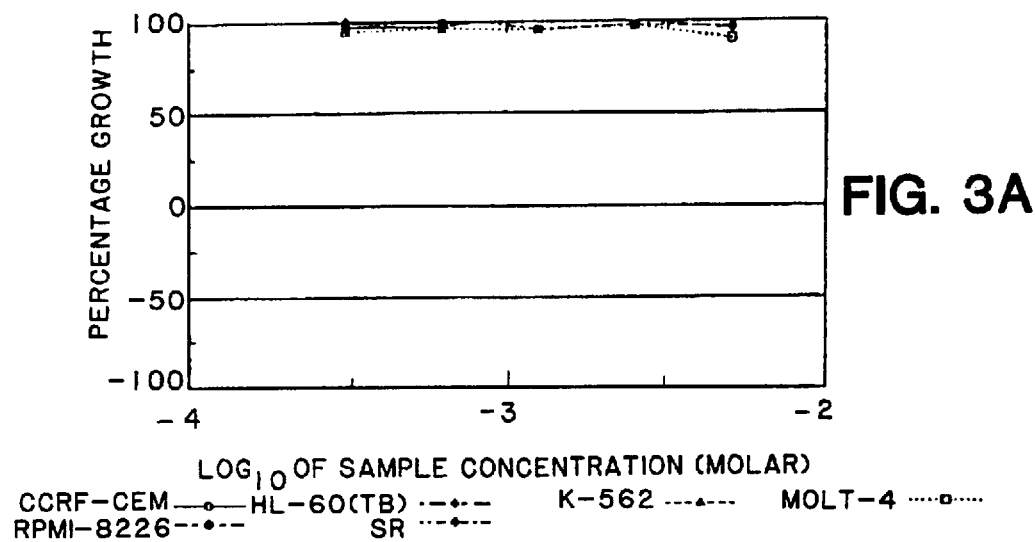
FIG. 3 Dose response curves of neoplastic cell lines treated with isobutyramide plotted for percentage of cell growth.
Figure 3B:
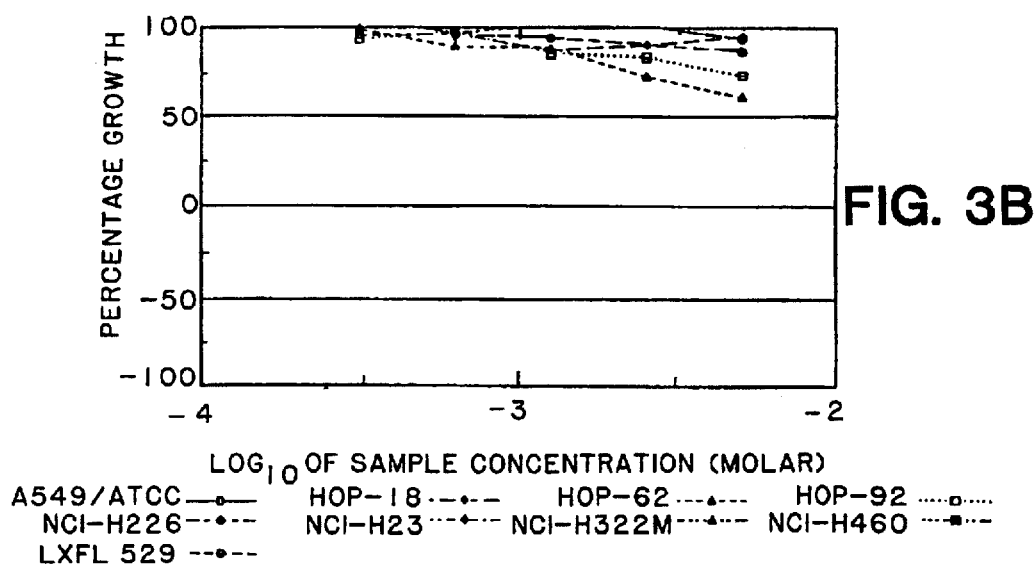
Figure 3C:
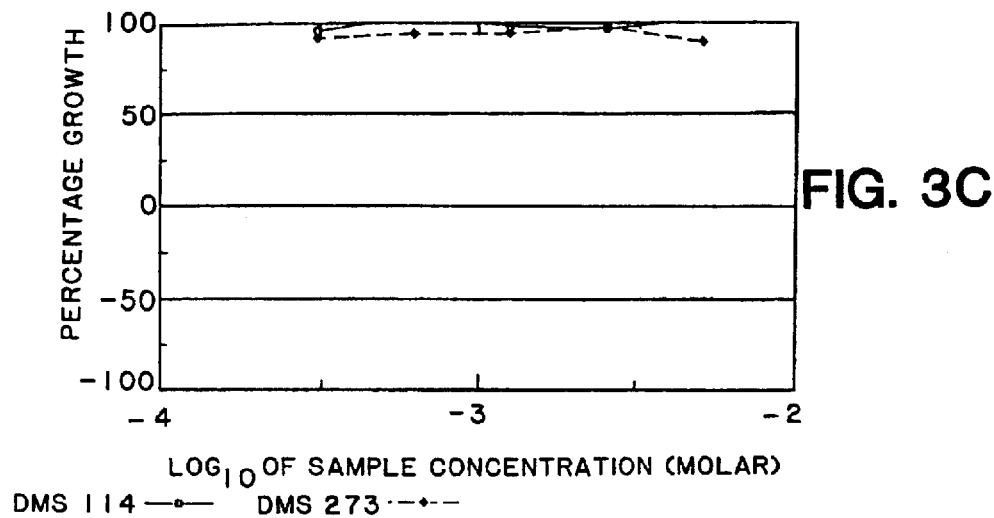
Figure 3D:
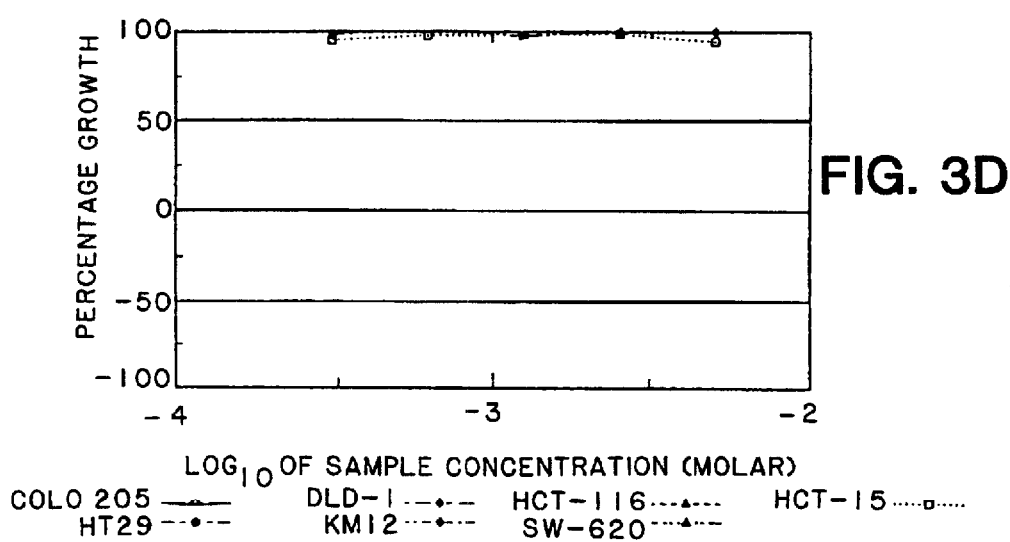
Figure 3E:
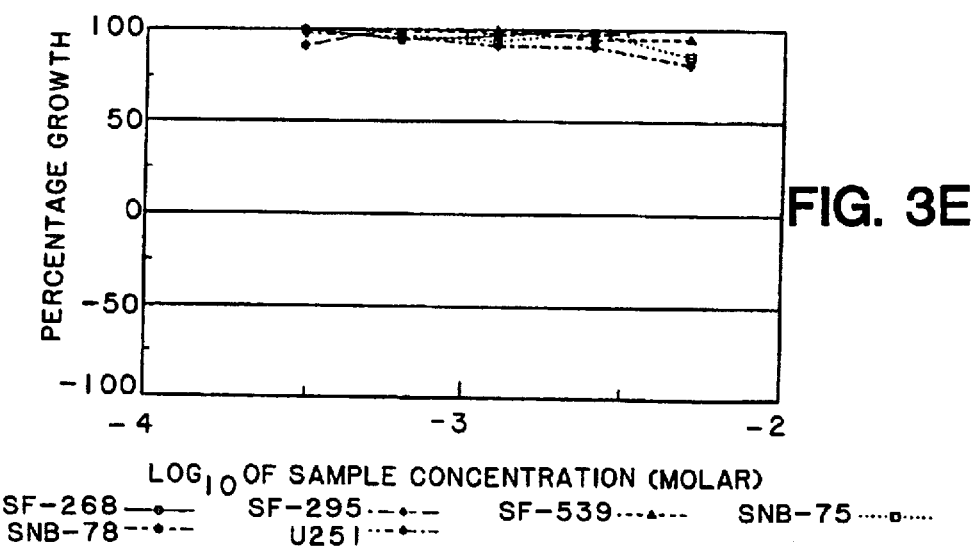
Figure 3F:
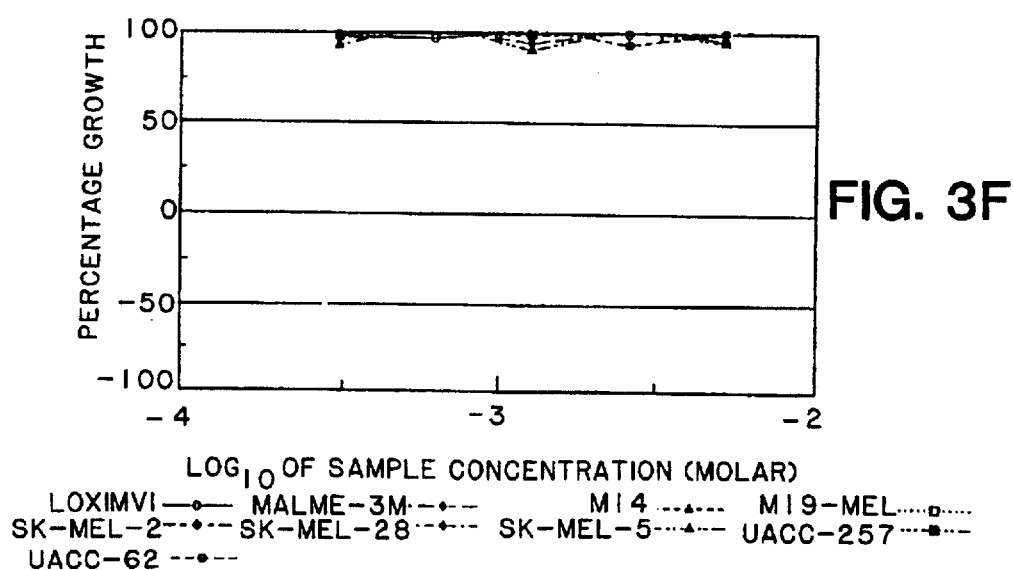
Figure 3G:
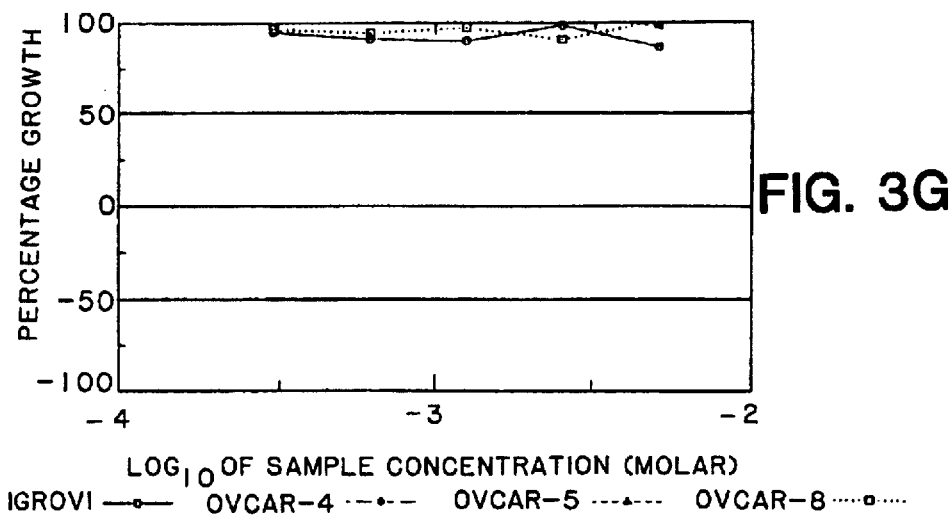
Figure 3H:
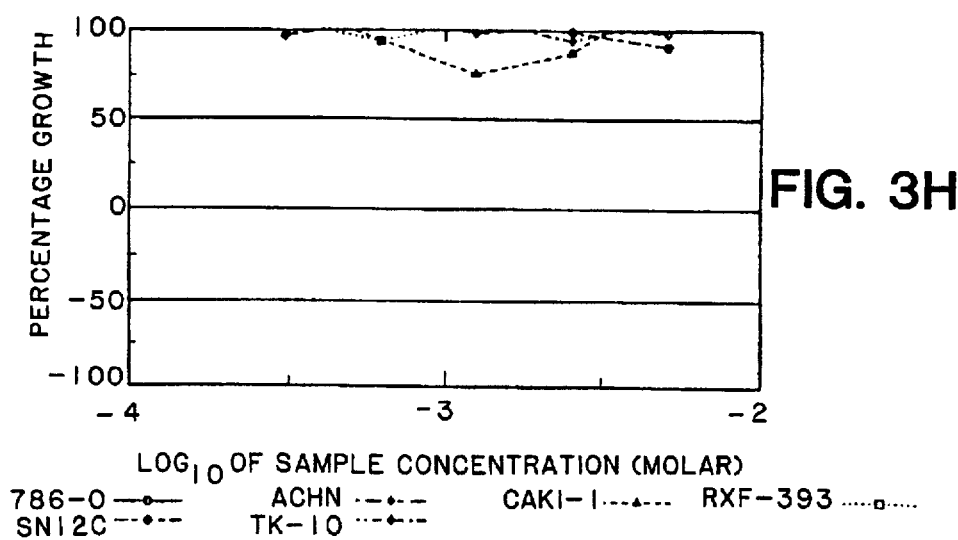
Figure 31:
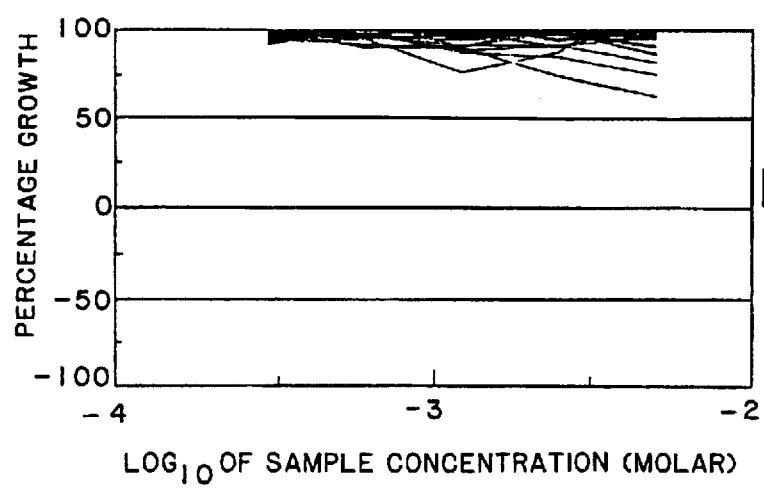
Figure 4A:
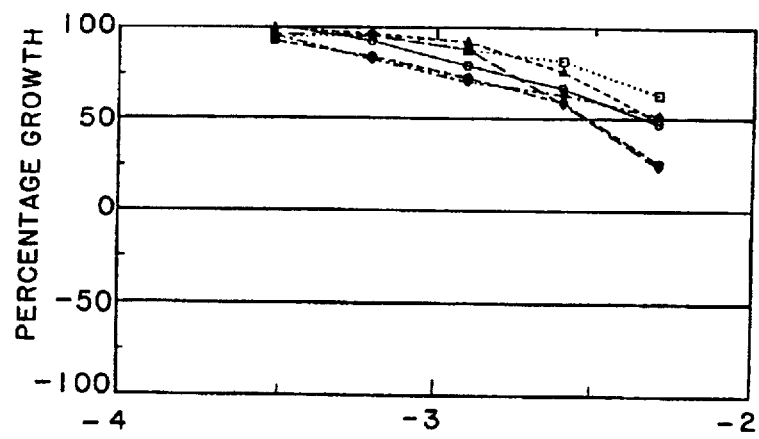
FIG. 4 Dose response curves of neoplastic cell lines treated with monobutyrin plotted for percentage of cell growth.
Figure 4B:
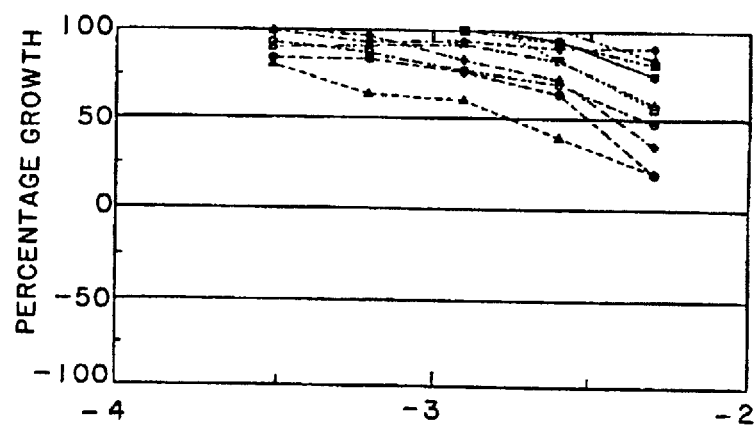
Figure 4C:
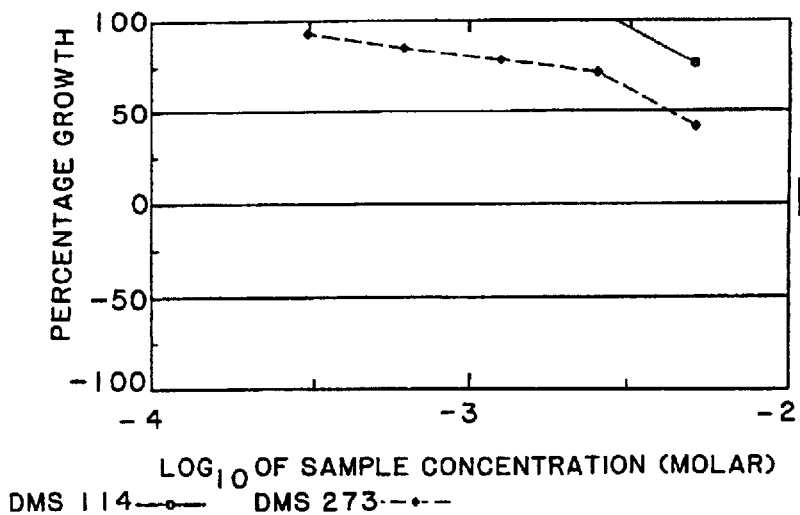
Figure 4D:
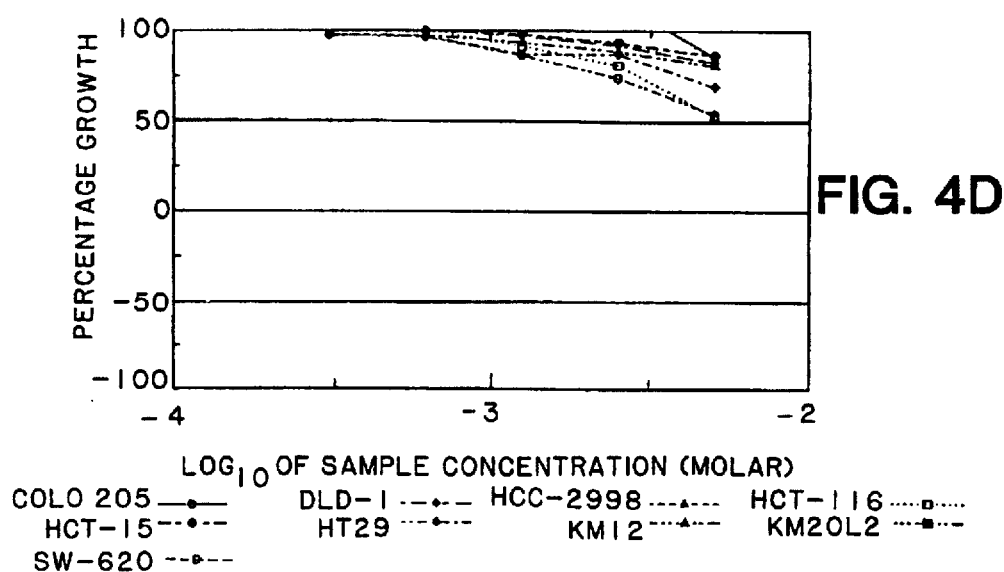
Figure 4E:
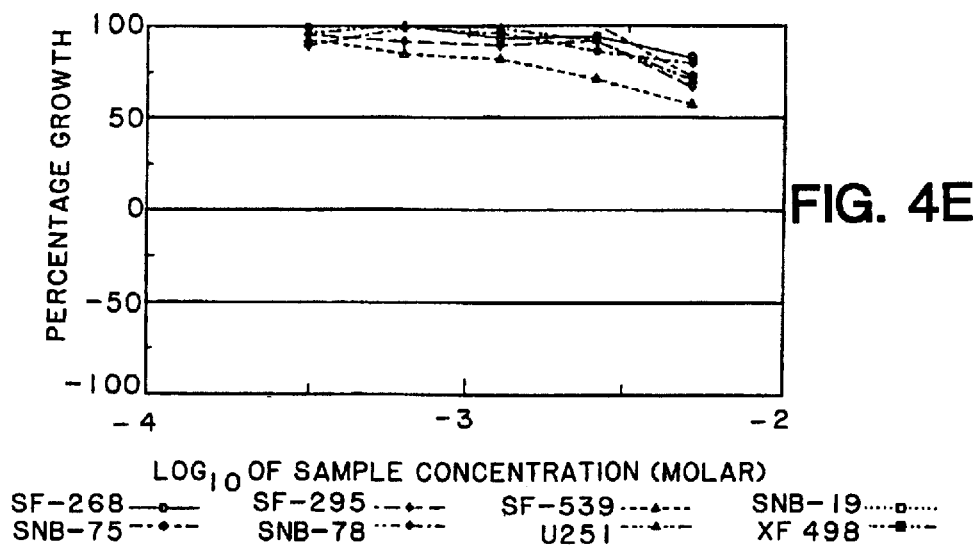
Figure 4F:
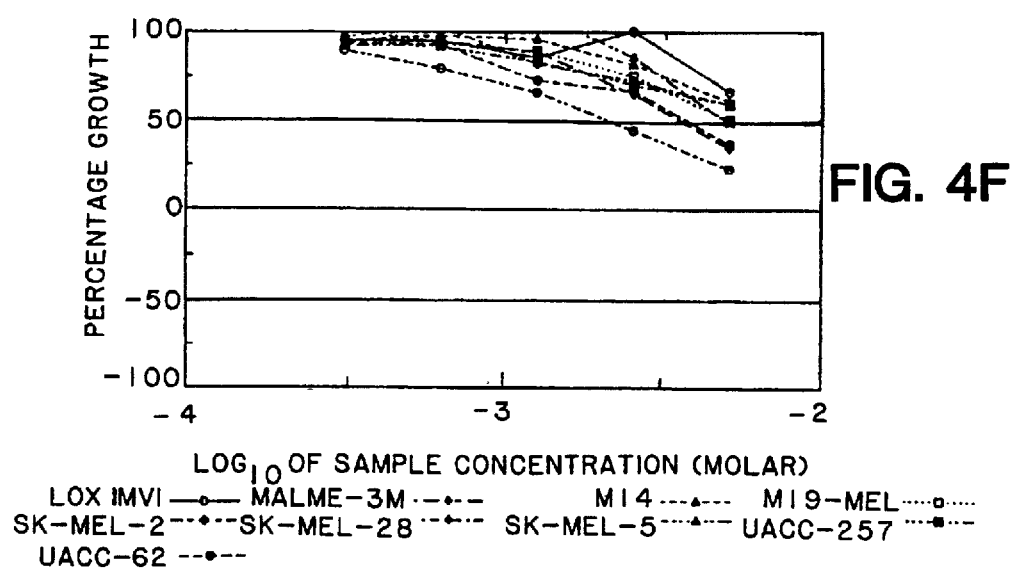
Figure 4G:
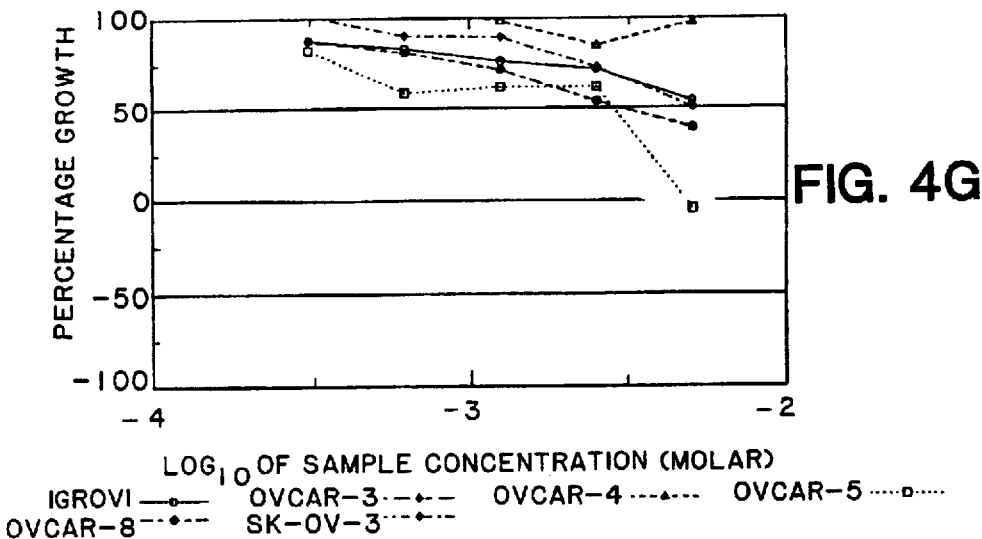
Figure 4H:
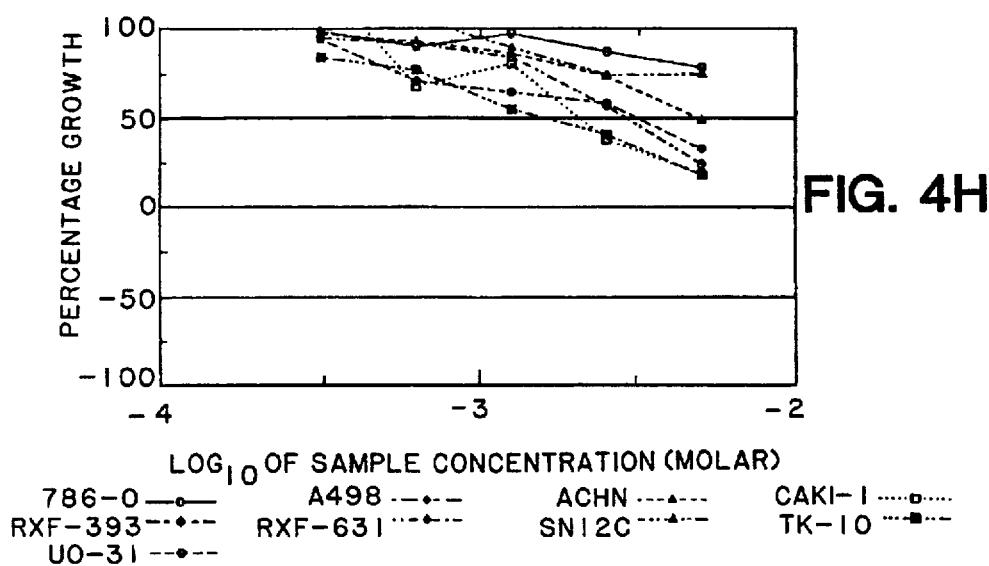
Figure 4I:
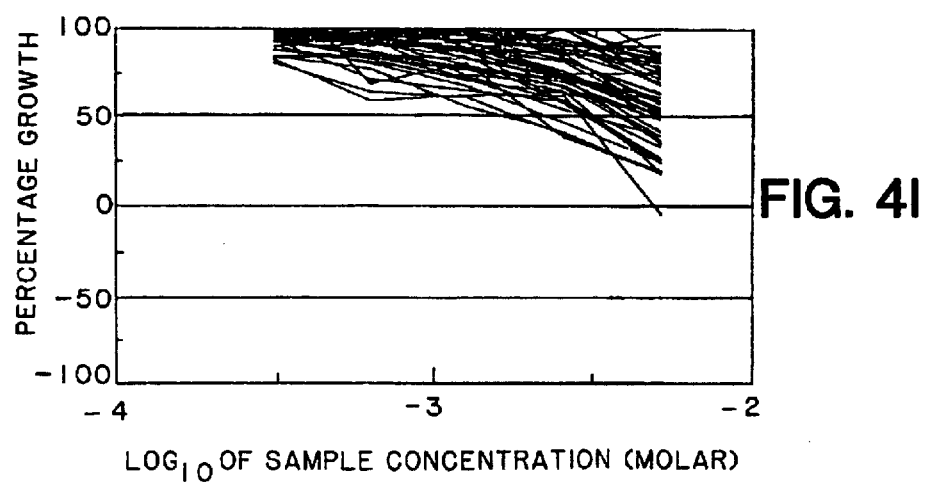
Figure 5A:
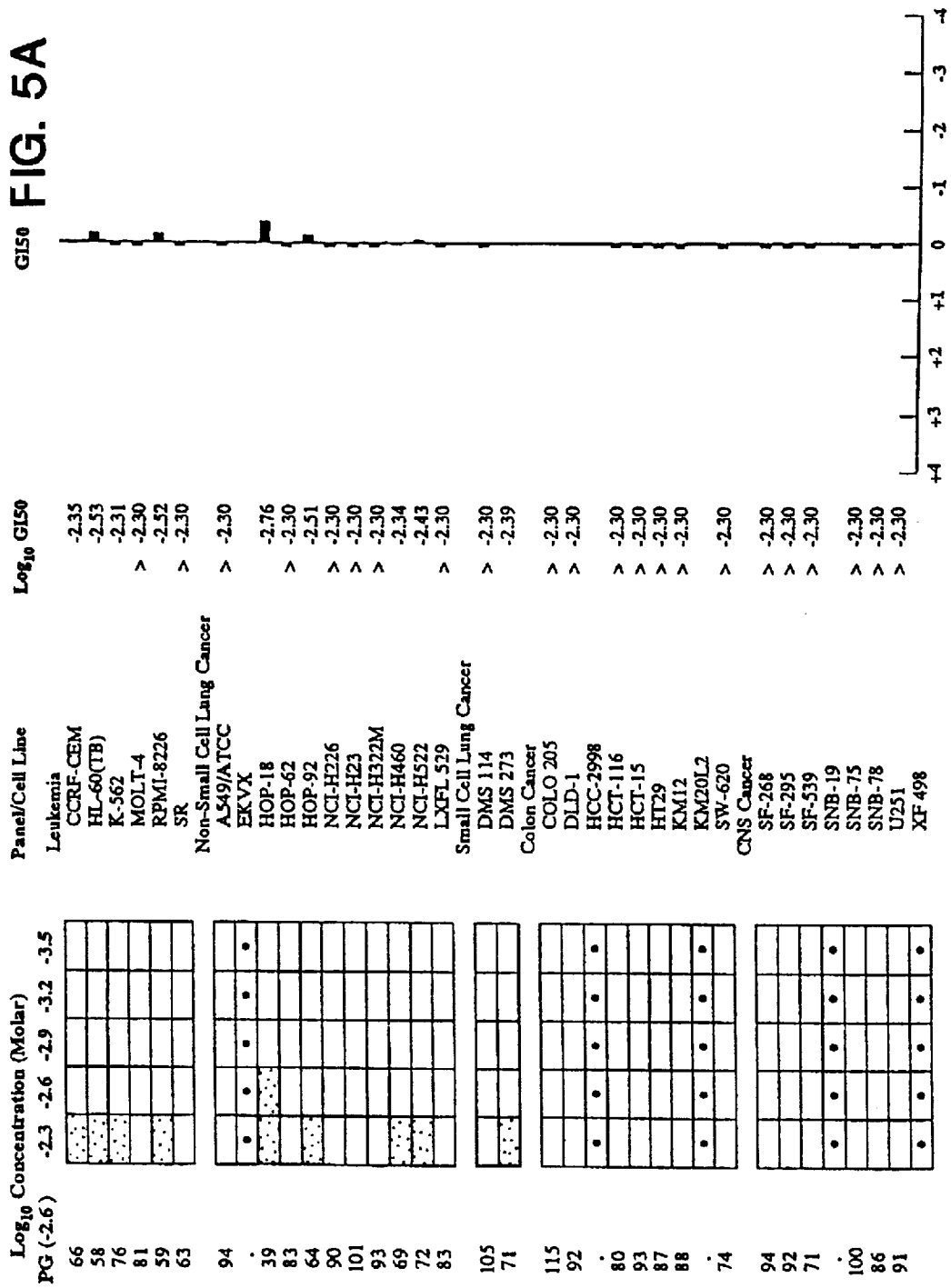
FIG. 5 Data from growth response curves indicating growth inhibition with monobutyrin.
Figure 6A:
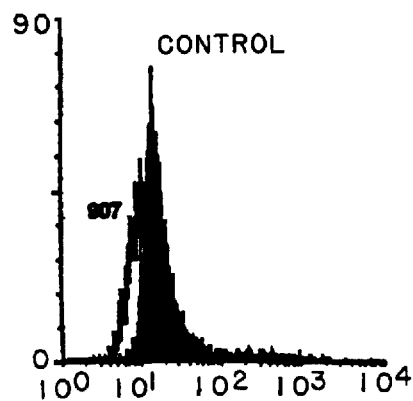
FIG. 6 FACS analysis of the levels of surface MHC antigen expression on K562 cells treated with 907, arginine butyrate, isobutyramide or 901.
Figure 6B:
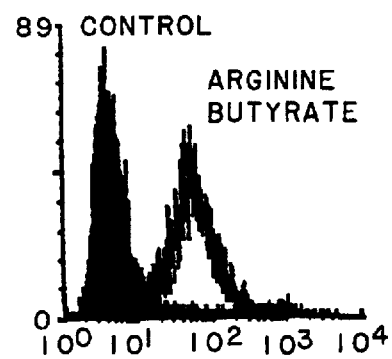
Figure 6C:
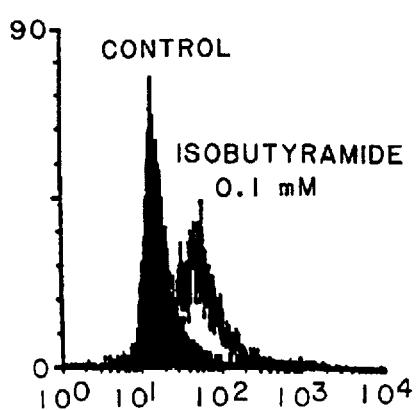
Figure 6D:
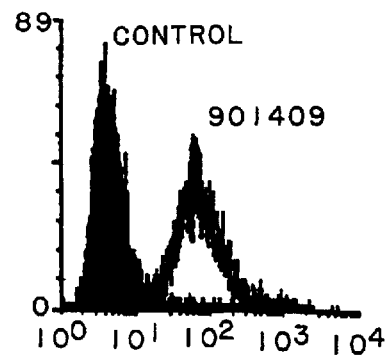
Figure 7A:
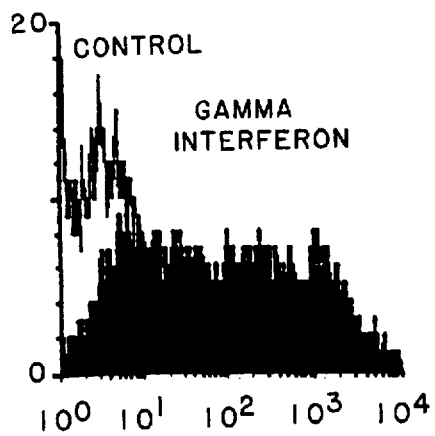
FIG. 7 FACS analysis of the levels of surface MHC antigen expression on K562 cells treated with γ-interferon, isobutyramide or monobutyrin.
Figure 7B:
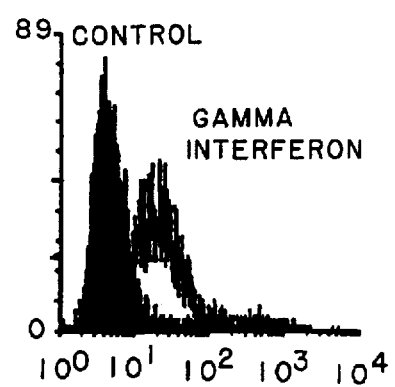
Figure 7C:
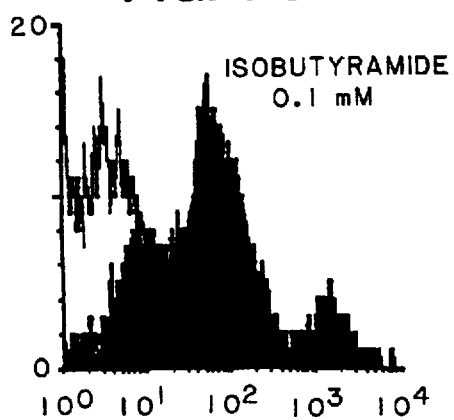
Figure 7D:
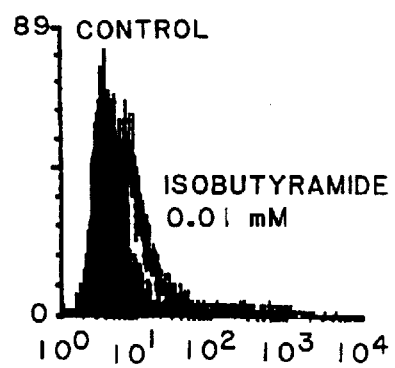
Figure 7E:
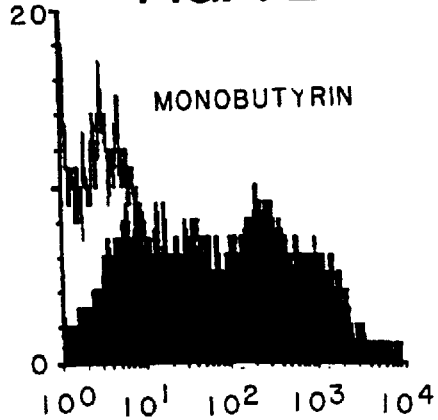
Figure 7F:
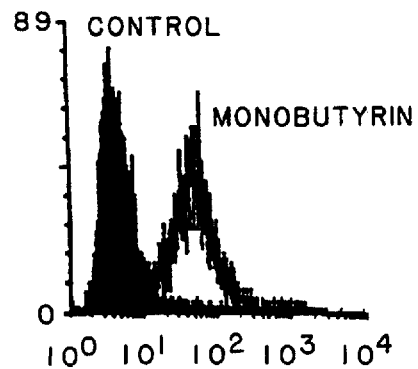

Isobutyramide, arginine butyrate and monobutyrin were screened for cytotoxic effects on a number of established tumor cells. Cytotoxicity, as measured in these studies, is not necessarily the same as growth inhibition or differentiation. These effects would not be expected to show up prominently in these assays. Arginine butyrate was found to have some cytotoxic activity against leukemia cells, melanoma cells, ovarian cancer cells, and breast cancer cells (FIGS. 1 and 2). The 50% lethal concentration ($LC_{50}$) of arginine butyrate on each of these cells was determined to be greater than 0.1 mM ($\log_{10} LC_{50} => -3.6$). Isobutyramide was found to have some cytotoxic activity against non-small cell lung cancer lines (FIG. 3). Monobutyrin was found to have some cytotoxic activity against leukemia cells, non-small cell lung cancer cells, small cell lung cancer cells, melanoma cells, ovarian cancer cells, and renal cancer cells (FIGS. 4 and 5). The $LC_{50}$ for isobutyramide on each cell line was determined to be greater than 1.0 mM ($\log_{10} LC_{50} => -2.3$).

Example 5

Differentiating Effects of Compounds on HT-29 Cells

Cultures of HT-29 cells were treated with arginine butyrate, isobutyramide and 3-phenyl butyrate. At concentrations of 5 mM, one marker for differentiation, alkaline phosphatase activity, was rapidly induced by all three compounds. At 2 mM concentrations, actively growing cultures of HT-29 cells were inhibited and arrested at days three and four with no further growth observed after 25 days. A brush border was observed suggesting maturation of the cells had occurred. The proto-oncogene c-myc was down-regulated within two hours after treatment and within six hours, incorporation of tritiated thymidine decreased. There was also an induction of the maturation specific enzymes sucrase and isomaltase.

Example 6

Effects of Compounds on Lymphocyte Proliferation

Compounds of the invention were tested for potential immuno-suppressive effects using the proliferation of human lymphocytes in a mixed lymphocyte reaction (MLR) or in culture with phytohemagglutinin (PHA) stimulated human lymphocytes. The lymphocytes were exposed to the mitogenic stimulus and the compounds for 48 hours, after which, $^3$H-thymidine was incorporated. Proliferation of lymphocytes in the MLR or PHA-stimulated reaction requires that a number of complex actions occur, including sequential interactions of lectins and lymphokines with cell surface receptors over many hours, and the autocrine synthesis and secretion of lymphokines by the lymphocytes. This is an extremely sensitive indicator of cytotoxicity of the compounds against normal (non-tumor) cells.

TABLE V

| Compound | Inhibitory Concentration ($\mu$M) | |
|---|---|---|
| | 100% | 50% |
| NaB | 2,500 | 400 |
| ArgB | 3,500 | 1,000 |
| MoB | 3,500 | 3,500 |
| 901409 | >850 | 100 |
| L-594515 | 500 | 75 |
| D-594516 | >2,500 | 800 |
| 907388 | >2,500 | 1,400 |
| 103038 | >2,500 | >2,500 |
| IBA | >5,000 | >2,500 |

Sodium butyrate, arginine butyrate, monobutyrin, 901409 (chloropropionic acid), isobutyramide, and the L-isomer of β-chloro-L-alanine-HCl exhibited potent growth inhibitory effects on the majority of the tumor cell lines tested. This effect was consistent at various serum concentrations. L-594, arginine butyrate, and monobutyrin were equally active to sodium butyrate, 901409 was 4–5 times more active than sodium butyrate, and isobutyramide was 10–20 times as active. None of these compounds were particularly toxic to non-tumor mesenchymal cells.

The most potent anti-tumor agents (sodium butyrate, arginine butyrate, monobutyrin, 901409, L-594515, isobutyramide) showed some inhibition of lymphocyte reactivity at very high concentrations, but there was a significant "therapeutic index" of toxicity for tumor cells that spares normal human mesenchymal cells and lymphocytes. This is unlike any other classic chemotherapeutic activity.

Some tumor cell lines used are not known to be "differentiate-able" in culture, so the mechanism of growth inhibition by these compounds is not known. Those agents exhibiting the most potent effects on tumor inhibition are in some cases distinct from the compounds which are most active in regulating fetal globin gene expression. Some of the compounds exhibiting potent anti-tumor effect (901409 and L-594) are next adjacent homologs of butyric acid.

Example 7

Class I MHC Induction by Compounds

A human erythroleukemia which does not express class I MHC antigens (K562) was treated with isobutyramide, arginine butyrate, or monobutyrin. Each of these substances produced an up-regulation of MHC antigen expression as determined by immunofluorescence with a monoclonal antibody specific for Class I MHC. Increases in MHC expression on mouse tumor cells and on human tumor cells (K562, Jurkat, HuT78) resulted in their recognition and destruction by mouse or human cytotoxic T lymphocytes (Flyer, et al, 1986; R. T. Maziarz, et al., Mol. Immunol. 27:135–42, 1990).

Example 8

Up-regulation of IL-2R by Compounds

Arginine butyrate, monobutyrin and isobutyramide were found to be capable of up regulating TAC (p55) expression on both T and B-cell human leukemia or lymphoma cells. Induction of IL2R is shown (Table VI) four days after addition of butyric acid salts or derivatives, after staining with a fluorescent antibody specific for the human IL-2R. Shown in cell surface fluorescence on a log scale, where every 15.5 unit increase is a doubling of cell surface IL-2R expression.

TABLE VI

| Cell Lines | Baseline | 0.5 mM | 1.0 mM | 2.0 mM |
|---|---|---|---|---|
| Arginine Butyrate | | | | |
| NALM6 | 14 | 57 | 68 | 65 |
| RAJI | 55 | 78 | 65 | 72 |
| CEM | 40 | 67 | | |
| Isobutyramide | | | | |
| NALM6 | 14 | 35 | 34 | 44 |
| RAJI | 55 | 75 | 75 | 69 |
| CEM | 40 | | 44 | |
| 3-Phenyl Butyrate | | | | |
| NALM6 | 14 | 32 | 29 | 45 |
| RAJI | 55 | 75 | 78 | 79 |
| CEM | 40 | | 51 | |

Other forms of butyric acid (3-phenyl butyrate), which were administered to animals safely, also induces an increase in IL-2R expression. Additional data has demonstrated that IL-2R expression can be modulated by butyric acid salts or derivatives in hematopoietic malignancies. These compounds increased the tumor cell's susceptibility to killing by IL-2R targeted fusion toxins.

Example 9

Inhibition of Multi-Drug Resistance Protein Activity

Expression of P-glycoprotein (Pgp), the protein responsible for the majority of multi-drug resistance in tumors, can be increased by butyric acid salts and derivatives in cell lines derived from tumors arising from cells which normally express Pgp. Although the Pgp level increased 25-fold after butyric acid treatment in SW620 human colon carcinoma cells, the intracellular accumulation of the chemotherapeutic agents vinblastine, adriamycin, and actinomycin D increased rather than decreased. Treatment of a Pgp-expressing multidrug-resistant SW620 subline with compositions of the invention resulted in active interference with Pgp function. Sodium butyrate, while increasing Pgp levels, inhibited the phosphorylation of Pgp. Time course studies revealed a tight relationship between decreased Pgp phosphorylation and increased vinblastine accumulation after butyrate treatment. Withdrawal of butyric acid increased Pgp phosphorylation while concurrently decreasing vinblastine accumulation.

Example 10

Induction of MHC Antigens on K562 Cells

FACS (fluorescent activated cell sorter) analysis was used to examine the levels of MHC antigen expression on K562 cells in culture before (control), and after treatment (24 hours of exposure) with arginine butyrate at 1.0 mM, isobutyramide at 2 different doses, 1.0 and 0.1 mM, 907388 at 1.0 mM, 901409 at 1.0 mM, monobutyrin at 1.0 mM, or gamma interferon at 1,000 U/ml. Results are depicted in FIGS. 6 and 7. 907 and the other chemical forms had no effect on MHC expression. Arginine butyrate, isobutyramide at 1.0 mM, 901409, monobutyrin, and gamma interferon all induced MHC expression by 10–50 fold. Isobutyramide at 0.1 mM induced MHC expression by five-fold.

Example 11

Regulatory Effects of Butyric Acid Derivatives on Leukemia and Lymphoma Cells

To define the cytotoxic/differentiation effects of butyrate and the butyrate derivatives arginine butyrate and isobutyramide on T and B cell leukemia lines and the cells from patients with chronic lymphocytic leukemia (CLL), cell viability was studied by the MIT assay and IL-2R expression was quantitated. Following a 72 hour exposure to 1 mM butyric acid, the percent survival of CEM, RAJI and NALM6 cells was 14–25% of control while the growth of HUT102 cells was relatively unaffected (90% of control). Freshly harvested lymphocytes from two CLL patients demonstrated 50% and 60% growth inhibition in the presence of 1 mM sodium butyrate. Arginine butyrate produced a similar degree of growth inhibition in the cell lines and patients' cells, while isobutyramide, in contrast, only modestly affected growth. IL-2R expression, measured using an IL-2-phycoerythrin fluorokine, increased following butyric acid and arginine butyrate 5-fold in NALM6 cells and 1.5–2 fold in RAJI and CEM cells. Isobutyramide similarly induced IL-2R expression on NALM6 cells and RAJI cells, but not on CEM cells. These results establish cytotoxic/differentiation effects for butyrate derivatives on T and B leukemia cell lines and fresh CLL cells. Thus, the induction of IL-2 receptors by these derivatives should prove to be clinically exploitable in combination with agents targeting IL-2R expressing cells.

Example 12

Pharmacokinetics of Compounds

Arginine butyrate was administered intravenously to patients, doses were between 10–50 g/kg body weight per day for periods of 5–21 days. Plasma levels of drug were determined from blood samples removed and assayed at various intervals and were comparable regardless of the method of administration. Peak plasma levels were in the range of about 0.3–5.0 mM in both animals (baboons) and humans. Serum half-life was determined to be about 15 minutes. All doses were generally well tolerated.

Isobutyramide was given orally to a number of patients. This compound is readily absorbed in the gastric mucosa and detectable levels of drug were present in primates and humans for greater than 24 hours after administration. Isobutyramide appeared in the plasma within 5–15 minutes of oral administration. Peak levels occurred at about 2 hours, and drug half-life was about 6.5–10.5 hours depending on the dose administered. In vitro and in vivo studies demonstrated that fetal globin synthesis, one biological effect, was stimulated or increased within 6 hours of exposure without adverse side effects.

Patient #1 received 50–150 mg/kg. Plasma levels ranged from 0.9 to 1.88 mM at two hours after administration and fell to about 0.4 mM between 15 to 22 hours after the last dose. Patient #2 received 100 mg/kg and after two hours had a drug level of 3.6 mM. Drug levels two hours after other dose were as follows: 10 mg/kg=0.24 mM; 25 mg/kg=0.44 mM; 60 mg/kg=0.93 mM; 75 mg/kg=1.29 mM. Trough levels at 12–13 hours after a dose ranged from 0.36 to 2.06 mM. Patient #3 received a single oral dose and had a drug serum level two hours after administration of 1.88 to 3.15 mM. Additional doses ranged between 60–100 mg/kg. Later doses of 75–100 mg/kg produced drug levels of 4.32 mM four hours after administration, 2.45 mM eight hours after administration, and drug was still detectable 24 hours after administration. Patient #4 received a single 50 mg/kg dose which produced serum drug levels of 1.55 mM at 1.5 hours, 1.42 mM at 2 hours, 1.16 mM at 4 hours, 0.67 at 8 hours and 0.49 mM at 12 hours. Patient #5 received oral doses of 25–100 mg/kg and at 2 hours had a drug level range of 0.4 mM to 2.6 mM. Drug levels accumulated even higher on multiple daily doses. All doses to all patients were generally well tolerated.

Example 13

Reduction of Leg Ulcer With Butyrate Treatment

A 22 year old female patient was treated continuously for 20 days with increasing doses (up to 2 g/kg body weight) of arginine butyrate intravenously. Within days of treatment, a leg ulcer which had not responded to conventional treatments including antibiotic creams and ointments, began to show signs of healing. After the full 20 days of treatment the ulcer had nearly completely healed, and later had completely healed. It has not recurred even after treatment was discontinued for over a year.

Example 14

Summary of Butyrate Experience in Patients with Refractory Neoplasms

Patient #1 (not related to patients of Example 11) with metastatic melanoma to the brain and skin had completed 1 cycle of 10 day infusion of Arginine Butyrate at 500 mg/kg/day, infused over 6–8 hours. The patient experienced increasing pain under the skin tumor nodules 12 hours after initiating the infusion, which lessened 36 hours after discontinuing the infusion after day 5. The patient's pain again worsened approximately 12 hours after initiation of infusion on day 6, but there was a reduced requirement for narcotics to control pain. This form of cancer is not typically associated with pain of the neoplastic cells, nor pain associated with infusion therapy. It was believed that treatment may have been having some effect. Up to the initiation of treatment, melanoma cell number had been continuing to increase as had the aggressiveness of metastasis. Evaluation 2 weeks after completion of the first cycle showed that metastatic lesions had not increased in size or number. There were no adverse effects upon the patient's organ function relating to the liver, kidneys, heart, lungs, gastrointestinal tract or bone marrow with the infusion of arginine butyrate.

Patient #2 has metastatic breast cancer. On day 1 of infusion of arginine butyrate 500 mg/kg/day, the patient reported symptoms of nausea and decreased appetite 18 hours prior to starting drug, and vomited once prior to starting the infusion. Four hours after initiating the infusion, the patient continued to have nausea, and vomited 5 times in spite of receiving antiemetics. The patient was admitted to the hospital for IV hydration and workup. The patient had several episodes of watery diarrhea for 2 days and nausea for 36 hours. There was a low grade fever (100.2° F.). Workup included C&S of blood, urine and diarrhea, head CT to R/O mets. The patient had been on a slow taper of prednisone prior to initiating arginine butyrate, and had the dose reduced 1 week prior to starting arginine butyrate. The patient had the dose of prednisone empirically increased to previous levels, and the nausea resolved within 12 hours. The patient has started a first cycle of arginine butyrate.

Patient #3 has metastatic colon cancer to the liver. This patient had completed two cycles of isobutyramide 400 mg/kg/day, 14 days each cycle. This drug course was complicated by emesis 15–30 minutes after taking the drug starting on day 4 of cycle 1. This postdose emesis continued in spite of a 25% and 50% dose reduction. The last 4 days of cycle 2 had success in keeping the drug down after patient finally filled a prescription for compazine, which was taken prior to ingesting the isobutyramide. During the course of therapy work-up of the emesis included evaluation for gastric obstruction/gastritis, and CNS mets which were negative. The patient experienced an increase of serum alkaline phosphatase during the two cycles, but other liver function tests remained stable. The patient also had progressive extremity weakness during the courses of isobutyramide. Work-up included MRI of the spine to R/O carcinomatous meningitis and serial EMG's, the latter which demonstrated patchy peripheral nerve demyelinating process. Review of the patients records suggested that the patient's neurological symptoms preceded initiation of isobutyramide. It was the opinion of the neurology service that these symptoms were a result of a chronic autoimmune demyelinating process, and not directly related to butyrates. The patient was given IV immunoglobulin as per recommendation of neurology service 1.5 weeks after completion of cycle 2 with improvement of EMG conduction, but no subjective improvement. Restaging of evaluable tumor after 2 cycles of isobutyramide demonstrated progression of tumor in the liver, and the patient was removed from the study. There were no adverse effects upon organ function noted in the liver, kidneys, lungs, heart, or bone marrow. The patient experienced grade 2 GI toxicity (2–5 episodes of emesis over 24 hours).

Example 15

Rat Ileal Loop Model of Inflammatory Bowel Disease

Rats were pretreated for three days with oral isobutyramide at 100 mg/kg/day. At the end of that period, five treated and five untreated animals had three ileal loops per animal surgically created. Lipopolysaccharide (LPS) was administered to incite the inflammatory response in the loops and two parameters were used to determine the extent of colitis; (1) fluid volume in the loops and (2) mannitol flux across the bowel. In the isobutyramide treated animals, there was an average of 40% reduction in fluid volume and mannitol flux in ileal loops, indicating that isobutyramide was responsible for moderating the inflammatory response.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

I claim:

1. A method for treating a wound in a patient in need thereof which comprises administering by oral or parenteral means a therapeutically-effective amount of a composition comprising as its active ingredient a compound selected from the group consisting of butyric acid and an amino acid, heptafluorobutyric acid, 3-chloropropionic acid, β-chloro-L-alanine hydrochloride and isobutyramide.

2. The method of claim 1, wherein said wound is an ulcer.

3. The method of claim 1, wherein said patient is a human.

4. The method of claim 1, wherein said compound is arginine butyrate.

5. The method of claim 2, wherein said compound is arginine butyrate.

6. The method of claim 1, wherein said active ingredient is selected from the group consisting of arginine butyrate and isobutyramide.

7. A method for treating a wound in a patient in need thereof which comprises administering by topical means a therapeutically-effective amount of a composition comprising as its active ingredient a compound selected from the group consisting of butyric acid and an amino acid, hepta-heptafluorobutyric acid, 3-chloropropionic acid, β-chloro-L-alanine hydrochloride and isobutyramide.

8. The method of claim 1, wherein said composition is administered intravenously at a therapeutically-effective amount of about 25 milligram per kilogram body weight per day to about 50 gram per kilogram body weight per day.

9. The method of claim 8, wherein said therapeutically effective amount is about 500 milligrams per killogram body weight per day to about 10 gram per kilogram body weight per day.

10. A method for treating a wound in a human patient in need thereof which comprises selecting a patient having a wound in need of treatment and administering by oral or parenteral means a therapeutically effective amount of a composition comprising as its active ingredient arginine butyrate.

11. The method of claim 10, wherein the wound is a refractory ulcer.

* * * * *

UNITED STATES PATENT AND TRADEMARK OFFICE
CERTIFICATE OF CORRECTION

| | |
|---|---|
| PATENT NO. | : 5,858,365 |
| APPLICATION NO. | : 08/473957 |
| DATED | : January 12, 1999 |
| INVENTOR(S) | : Susan P. Perrine |

Page 1 of 1

It is certified that error appears in the above-identified patent and that said Letters Patent is hereby corrected as shown below:

On the Title Page of the Patent, Reference [75] Inventor: Douglas V. Faller, Braintree, MA should appear as follows:
        [75] Inventor: Susan P. Perrine, Weston, MA Signed and Sealed this Twenty-second Day of January, 2008

JON W. DUDAS
*Director of the United States Patent and Trademark Office*